United States Patent
Burke et al.

(10) Patent No.: US 11,732,238 B2
(45) Date of Patent: Aug. 22, 2023

(54) MAIN-CHAIN LIQUID CRYSTALLINE HYDROGELS FOR CELL CULTURE

(71) Applicant: University of Connecticut, Farmington, CT (US)

(72) Inventors: Kelly Anne Burke, Sutton, MA (US); Yongjian Wang, Monroe, NJ (US)

(73) Assignee: University of Connecticut, Farmington, CT (US)

( * ) Notice: Subject to any disclaimer, the term of this patent is extended or adjusted under 35 U.S.C. 154(b) by 156 days.

(21) Appl. No.: 17/307,808

(22) Filed: May 4, 2021

(65) Prior Publication Data
US 2021/0348122 A1  Nov. 11, 2021

Related U.S. Application Data

(60) Provisional application No. 63/033,575, filed on Jun. 2, 2020, provisional application No. 63/019,943, filed on May 4, 2020.

(51) Int. Cl.
*C12N 5/00* (2006.01)
*C12N 5/0775* (2010.01)
*C09K 19/34* (2006.01)

(52) U.S. Cl.
CPC .......... *C12N 5/0068* (2013.01); *C09K 19/348* (2013.01); *C12N 5/0662* (2013.01); *C12N 2513/00* (2013.01); *C12N 2533/30* (2013.01); *C12N 2537/10* (2013.01); *C12N 2539/00* (2013.01)

(58) Field of Classification Search
CPC .............. C12N 5/0062; C12N 2537/10; C12N 2533/30; C09K 19/348
See application file for complete search history.

(56) References Cited

U.S. PATENT DOCUMENTS

| | | |
|---|---|---|
| 9,994,812 B2 | 6/2018 | Kim et al. |
| 10,435,734 B2 | 10/2019 | Kim et al. |
| 2019/0040110 A1 | 2/2019 | Ittah et al. |
| 2019/0380823 A1 | 12/2019 | Schwartz et al. |

OTHER PUBLICATIONS

USPTO structure search, published on Mar. 2023.*
"Agrawal et al., "Electromechanically Responsive Liquid Crystal Elastomer Nanocomposites for Active Cell Culture", ACS Macro Lett., 2016, 5, pp. 1386-1390."
Agrawal et al., "Stimuli-Responsive Liquid Crystal Elastomers for Dynamic Cell Culture", J. Mater. Res., 2015, 30, pp. 453-462.
Bera et al., "Liquid Crystal Elastomer Microspheres as Three-Dimensional Cell Scaffolds Supporting the Attachment and Proliferation of Myoblasts", ACS Appl. Mater. Interfaces 2015, 7, pp. 14528-14535.
Boothby et al., "Molecularly-ordered hydrogels with controllable, anisotropic stimulus response," Soft Matter, 2019,15, pp. 4508-4517.
Ferrantini et al., "Development of Light-Responsive Liquid Crystalline Elastomers to Assist Cardiac Contraction", Circ. Res., 2019, 124, pp. e44-e54.
Herrera-Posada et al., "Magneto-Responsive Liquid Crystalline Elastomer Nanocomposites as Potential Candidates for Dynamic Cell Culture Substrates", Mater. Sci. Eng., C 2016, 65, pp. 369-378.
Kim et al., "Preparation of Monodomain Liquid Crystal Elastomers and Liquid Crystal Elastomer Nanocomposites", J. Visualized Exp., 2016, No. 108, No. e53688.
Martella et al., "Liquid CrystalInduced Myoblast Alignment", Adv. Healthcare Mater., 2019, vol. 8, 10 pages.
Martella et al., "Liquid Crystalline Networks toward Regenerative Medicine and Tissue Repair", Small, 2017, 13, 1702677, 8 pages.
Prevot et al., "Liquid Crystal Elastomer Foams with Elastic Properties Specifically Engineered as Biodegradable Brain Tissue Scaffolds", Soft Matter, 2018, vol. 14, pp. 354-360.
Prevot et al., "Synthesis of Biocompatible Liquid Crystal Elastomer Foams as Cell Scaffolds for 3D Spatial Cell Cultures", J. Visualized Exp., 2017, No. 122, No. e55452.
Safinya et al., "Assembly of Biological Nanostructures: Isotropic and Liquid Crystalline Phases of Neurofilament Hydrogels," Annual Review of Condensed Matter Physics, 2015, vol. 6, No. 1, pp. 113-136.
Sharma et al., "Biocompatible, Biodegradable and Porous Liquid Crystal ElastomerScaffolds for Spatial Cell Cultures", Macromol. Biosci., 2015, 15, pp. 200-214.
Somkamnerd et al., "Micropatterned Cell Orientation of Cyanobacterial Liquid-Crystalline Hydrogels," ACS Appl. Mater. Interfaces 2018, vol. 10, No. 51, pp. 44834-44843.
Stumpel et al., "Stimuli-Responsive Materials Based on Interpenetrating Polymer Liquid Crystal Hydrogels," Advanced Functional Materials, 2015, vol. 25, No. 22, pp. 3314-3320.
Wang et al., "Soft Matter Phase Behavior of MainChain Liquid Crystalline Polymer Networks Synthesized by Alkyne-Azide Cycloaddition Chemistry", Soft Matter, 2018, 14, pp. 9885-9900.

* cited by examiner

*Primary Examiner* — Gregory Listvoyb
(74) *Attorney, Agent, or Firm* — Michael Best & Friedrich LLP

(57) ABSTRACT

Provided are polymers, which may be crosslinked to form a main-chain liquid crystalline (LC) hydrogel with a three-dimensional network. Also provided are methods of using the hydrogel as a substrate for tissue culture. For example, the hydrogel may organize into LC phases and encapsulate a plurality of cells within its polymeric network. In some embodiments, human stem cells are cultured using the present method with good viability and demonstrate faster proliferation in the present LC hydrogel compared to a non-LC gel.

20 Claims, 11 Drawing Sheets

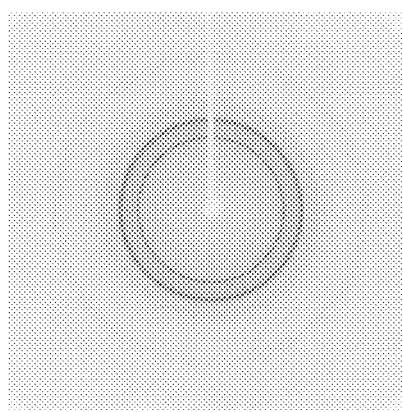
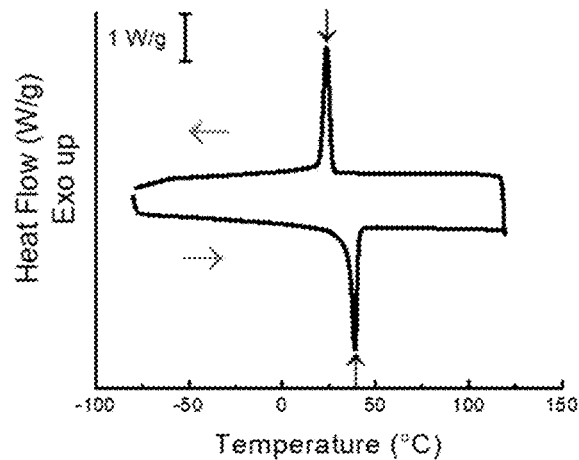
FIG. 7A  FIG. 7B
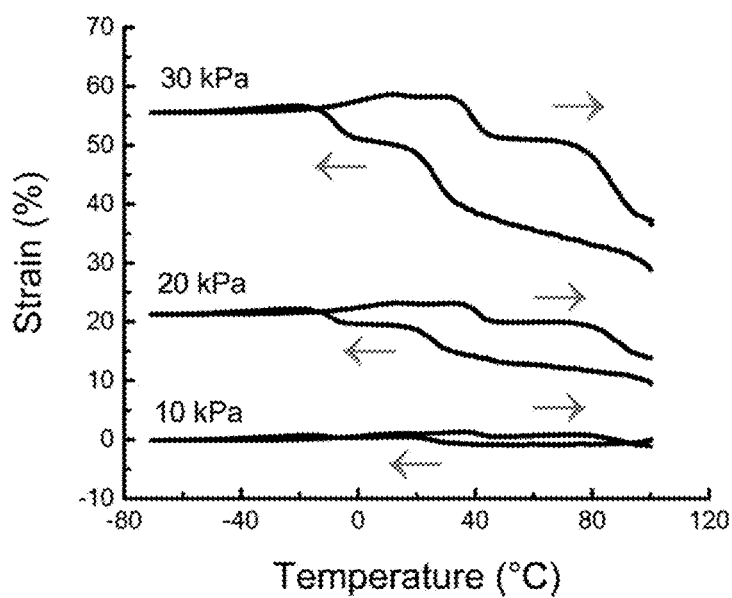
FIG. 8

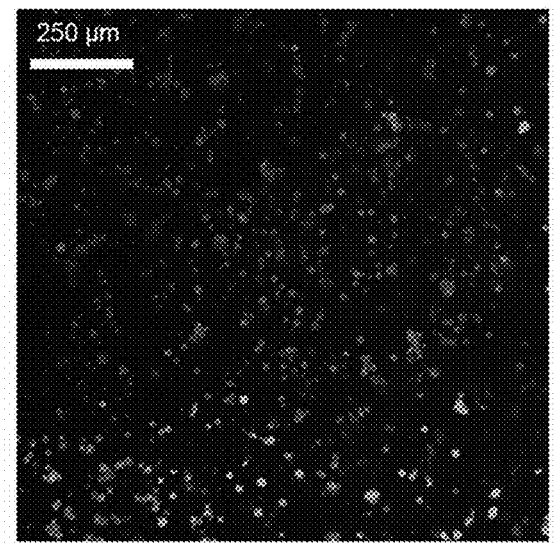
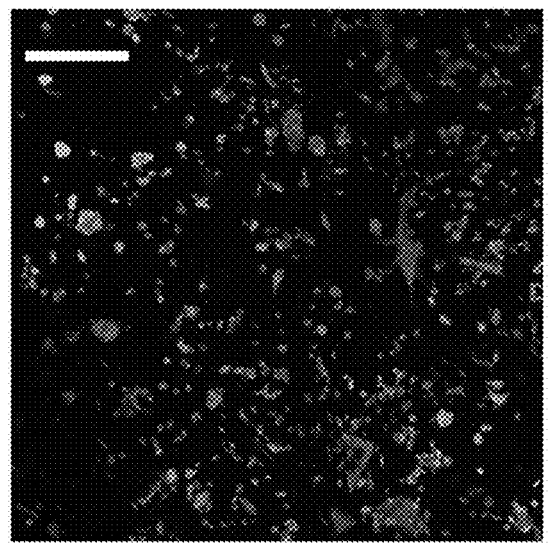
FIG. 14A                    FIG. 14B
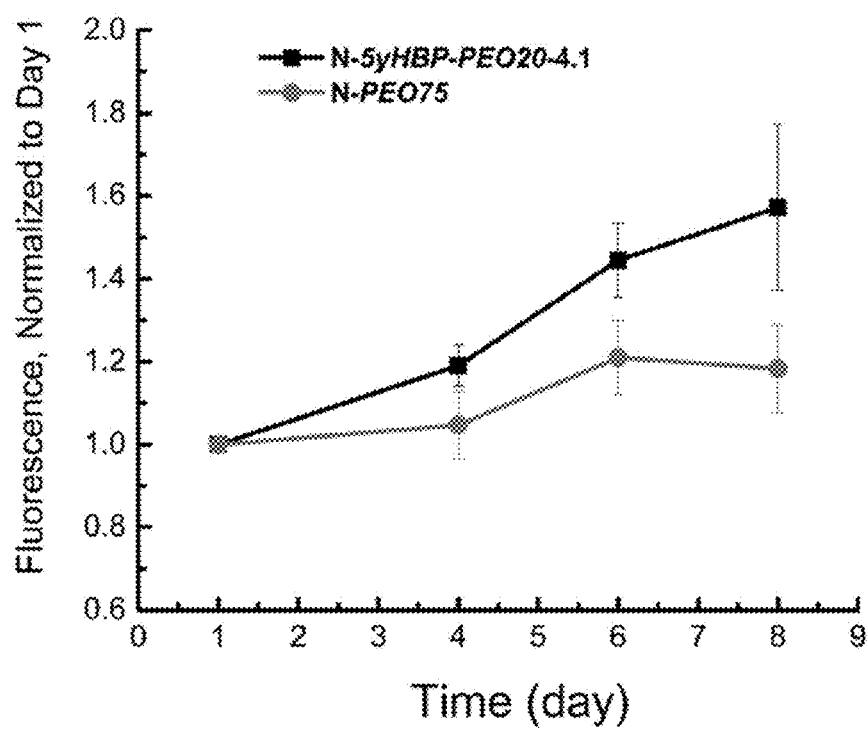
FIG. 15

MAIN-CHAIN LIQUID CRYSTALLINE HYDROGELS FOR CELL CULTURE

CROSS-REFERENCE TO RELATED APPLICATION

This application claims the benefit of and priority to U.S. Provisional Application No. 63/019,943, filed on May 4, 2020, and U.S. Provisional Application No. 63/033,575, filed on Jun. 2, 2020, the entire contents of all of which are hereby incorporated by reference.

INTRODUCTION

To regenerate soft tissues that have been damaged by trauma or disease, polymer constructs are often employed as substrates to support cell attachment, growth, and, ultimately, new tissue formation. A diverse library compositions and properties is available for biomaterials, but regardless of in vitro or in vivo application, a common goal is to develop cultures and/or tissues that function more like native tissues. Towards this end, studies have reported functional differences in cells and tissues formed in three-dimensional (3D) substrates (e.g., scaffolds and gels) compared to two-dimensional (2D) substrates (e.g., films). As cells form focal adhesions (FA) to interact with their surroundings, some of the functional differences observed between 2D and 3D cultures may arise because cellular interactions in a 3D space may be more relevant than interactions with a 2D substrate.

In terms of 3D culture substrates, hydrogels are an attractive format for soft tissues because their mechanical properties may be tuned to better match the mechanics of tissues and their high water content facilitates rapid nutrient and waste transport. However, encapsulating cells within a 3D matrix is not without its challenges. Cell-compatible chemistry and solvent systems are required, and gelation kinetics must be tuned to enable the distribution of cells within the gel without the loss of viability. Another key challenge is that, while anisotropy has been found in many tissues (e.g., skin, skeletal muscle, blood vessels, cartilage) and ordering been found to precede the assembly of structural proteins like collagen, existing physically and chemically-cross-linked hydrogels lack capability to effectively generate and control order in the absence of external forces (e.g., the application of mechanical forces or magnetic fields) or without the use of directional diffusion, patterning, or printing techniques.

Liquid crystalline (LC) materials exist in states between solid and liquid (i.e., as ordered liquids) known as liquid crystalline phases. LC materials contain rigid molecules called mesogens that organize into LC phases, where the mesogen orientation is described by an imaginary vector known as the director. End-capping calamitic (rod shaped) mesogens with reactive sites permits their incorporation into the polymer backbone, resulting in a main-chain LC polymer architecture. Main-chain LC polymers (LCPs) and networks (LCNs) directly couple polymer elasticity with molecular ordering, which is tunable into complex patterns by processing, leading to anisotropic and stimuli-responsive properties. As an example, LCNs reversibly extend and contract when cycling through the LC order-disorder transition through a process called actuation. The application of LCNs as cell culture substrates has primarily focused on exploiting actuation in two-dimensional (2D) culture on films or in three-dimensional (3D) culture on solid scaffolds. Although these LCNs have shown good biocompatibility, ordered microstructure and tunable mechanical properties, the hydrophobic nature of uncharged, calamitic liquid crystalline monomers and their polymers has hindered their use in hydrogels that permit 3D cell encapsulation. In a previous report, main-chain polyether-based LCNs were polymerized using a one step, copper-catalyzed alkyne-azide cycloaddition reaction, resulting in LCNs that maintained a LC phase even when hydrated in water up to 148%. While this work suggested the ability for LCNs to be used as hydrogels, the use of a copper catalyst and an organic solvent to dissolve the reactants precluded the encapsulation of cells within the swollen networks.

Thus, there remains a need for hydrogels having a liquid crystalline phase suitable for use as scaffolds for cell or tissue culture, in particular those materials that maintain the order and function of encapsulated cells and matrix proteins.

SUMMARY

In one aspect, the present disclosure provides a polymer of formula (I),

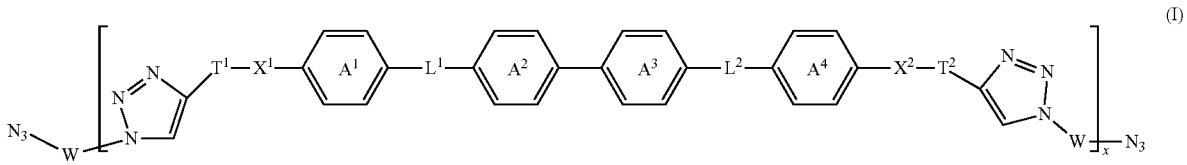

wherein $A^1$, $A^2$, $A^3$, and $A^4$ are each independently a phenyl optionally substituted with 1, 2, 3, or 4 $R^a$;

$L^1$, $L^2$, $X^1$, and $X^2$ are each independently O, NH, C(O), C(O)O, C(O)NH, or OC(O)NH;

$T^1$ and $T^2$ are each independently $C_{1-6}$alkylene;

W is $W^0$-L; wherein $W^0$ is selected from the group consisting of a polyether, a polyester, a polyamide, a polysiloxane, a polyurethane, and a combination thereof; and wherein L is a bond or —S—S—;

$R^a$ at each occurrence is independently —$NH_2$, —OH, —COOH, —CHO, halogen, cyano, —Oalkyl, —NHalkyl, —N(alkyl)$_2$, —C(O)alkyl, —C(O)Oalkyl, —OC(O)alkyl, —C(O)NHalkyl, —NHC(O)alkyl, or an alkyl optionally substituted with —$NH_2$, —OH, —COOH, or —CHO; and x is 1 to 100.-

In another aspect, the present disclose provides a cross-linked polymer comprising a moiety of formula (II),

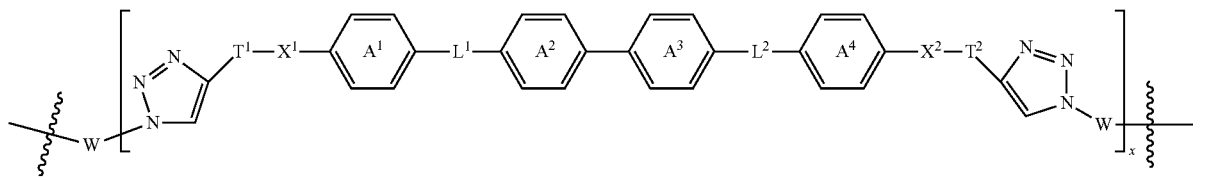

(II)

wherein $A^1$, $A^2$, $A^3$, and $A^4$ are each independently a phenyl optionally substituted with 1, 2, 3, or 4 $R^a$;

$L^1$, $L^2$, $X^1$, and $X^2$ are each independently O, NH, C(O), C(O)O, C(O)NH, or OC(O)NH;

$T^1$ and $T^2$ are each independently $C_{1-6}$alkylene;

W is $W^0$-L; wherein $W^0$ is selected from the group consisting of a polyether, a polyester, a polyamide, a polysiloxane, a polyurethane, and a combination thereof; and wherein L is a bond or —S—S—;

$R^a$ at each occurrence is independently —NH₂, —OH, —COOH, —CHO, halogen, cyano, —Oalkyl, —NHalkyl, —N(alkyl)₂, —C(O)alkyl, —C(O)Oalkyl, —OC(O)alkyl, —C(O)NHalkyl, —NHC(O)alkyl, or an alkyl optionally substituted with —NH₂, —OH, —COOH, or —CHO;

x is 1 to 100; and at least one terminal indicated by ⁓⁓⁓ is attached to a crosslinker.

In yet another aspect, the present disclosure provides a method of culturing a plurality of cells, comprising crosslinking a polymer as described herein by a crosslinker in a medium in which the cells are dispensed, thereby forming a three-dimensional network of the crosslinked polymer and encapsulating the cells in the three-dimensional network; and culturing the encapsulated cells.

BRIEF DESCRIPTION OF THE DRAWINGS

FIG. 2A shows DSC first heating trace of the 5yHBP mesogen (arrows added to highlight transition), and FIG. 2B shows thermogravimetric analysis of the 5yHBP mesogen.

(FIG. 3A), 130° C. (FIG. 3B), and 220° C. (FIG. 3C). There is no overall orientation of the liquid crystalline director in the images.

(FIG. 4B), 90° C. (FIG. 4C), 110° C. (FIG. 4D). There is no overall orientation of the liquid crystalline director in the images.

FIG. 6A shows DSC second heating trace of N-5yHBP-PEO20-4.1, and FIG. 6B shows tensile storage modulus and tan delta as a function of temperature for N-5yHBP-PEO20-4.1. Tick marks added to DSC trace to highlight transitions.

FIG. 7A shows 2D WAXS pattern of dry N-PEO75 measured at 25° C. FIG. 7B shows DSC second heating and cooling traces of dry N-PEO75. Vertical arrows were added to highlight transitions.

FIG. 8 shows thermomechanical actuation of N-5yHBP-PEO20-4.1 measured at different stresses.

FIG. 9A shows 2D wide angle scattering (WAXS) of dry N-5yHBP-PEO20-4.1 (at 25° C.). FIG. 9B shows 2D small angle scattering (SAXS) of dry N-5yHBP-PEO20-4.1 (at 25° C.). FIG. 9C shows 1D SAXS patterns of dry N-5yHBP-PEO20-4.1 measured at the temperatures noted therein. The data shown in (b) is the 25° C. trace in (c).

(FIG. 10A), 37° C. (FIG. 10B), and 55° C. (FIG. 10C).

FIG. 12A shows the result of N-5yHBP-PEO20-4.1, and FIG. 12B shows the result of N-PEO75.

FIGS. 14A and 14B show live and dead staining of human mesenchymal stem cells that were encapsulated and cultured in gels for 24 h. FIG. 14A shows the result of cells in N-5yHBP-PEO20-4.1 (a LC hydrogel), and FIG. 14B shows the result of cells in N-PEO75 (a non-LC hydrogel).

FIG. 15 shows metabolic activity measured as a function of time for hMSC encapsulated within N-5yHBP-PEO20-4.1 (a LC hydrogel) and N-PEO75 (a non-LC hydrogel). Fluorescence was measured and normalized relative to Day 1 values (Day 1 is 24 h post-encapsulation).

DETAILED DESCRIPTION

Figure 1:
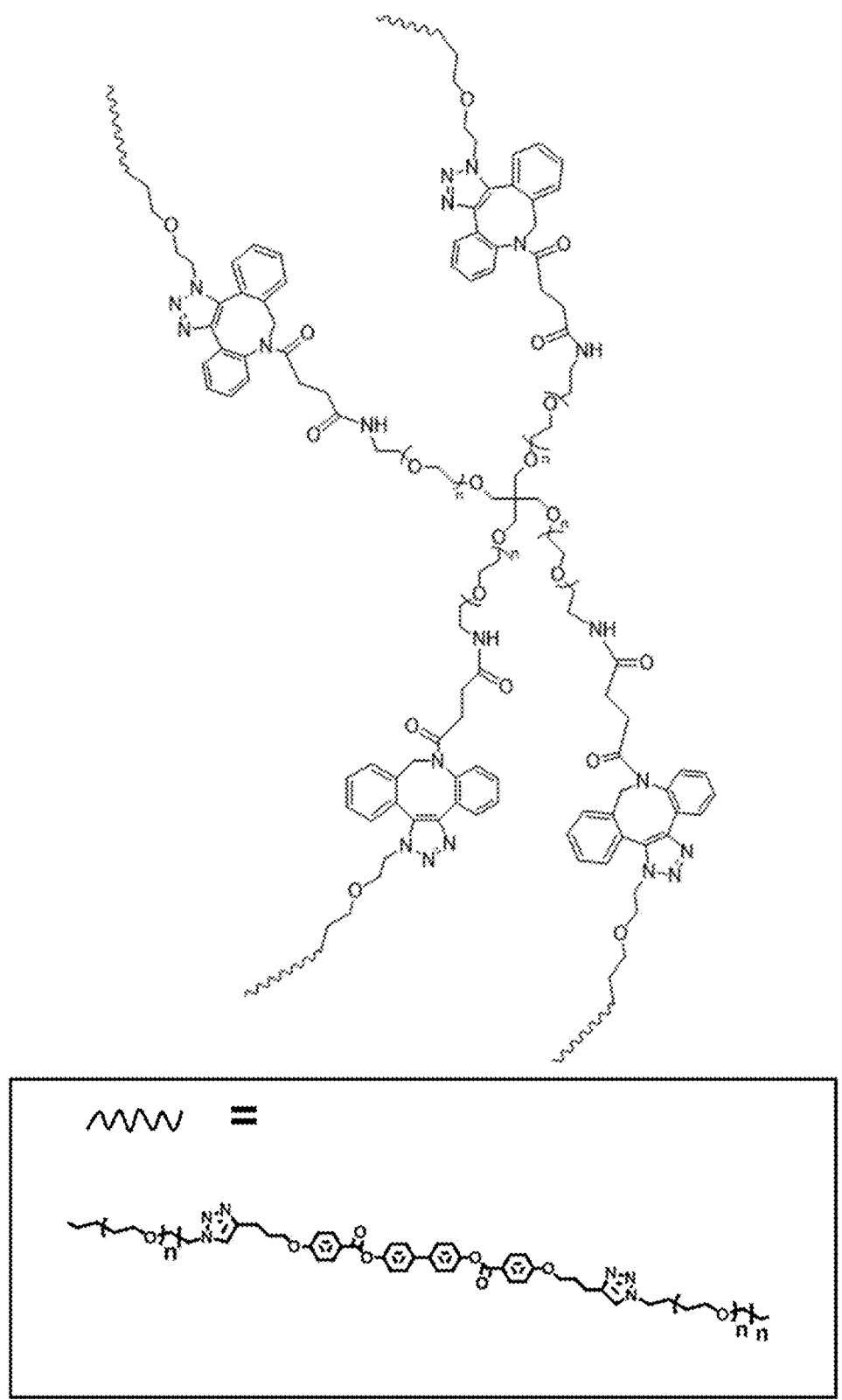
FIG. 1 shows a representative structure of the network resulting from the crosslinking of azide-terminated liquid crystalline polymers with DBCO. The wavy lines represent the polymer structure shown in the box.

The present disclosure relates to synthesis and characterization of main-chain calamitic liquid crystalline hydrogels, a new platform of materials that may support the encapsulation of human cells. The hydrogels described herein demonstrate that cell behavior may be affected by LC mesophases in 3D culture.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched chain saturated hydrocarbon. The alkyl may contain from 1 to 20 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —$CH_2CH_2$—, —$CH_2CH_2CH_2$—, —$CH_2CH_2CH_2CH_2$—, and —$CH_2CH_2CH_2CH_2CH_2$—.

The term "crosslinker" as used herein refers to a molecule or a function group capable of linking one polymer to another polymer, or one part of a polymer to another part of the polymer, via formation of one or more chemical bonds between the two polymers or the two parts of the polymer.

The term "chemically bonding" or "chemically attaching" as used herein refers to forming a chemical bond between two substances. The chemical bond may be an ionic bond, a covalent bond, dipole-dipole interaction, or hydrogen bond.

The term "halogen" as used herein, means Cl, Br, I, or F.

In some instances, the number of carbon atoms in a hydrocarbyl substituent (e.g., alkyl or alkylene) is indicated by the prefix "$C_{x-y}$" or "$C_x$-$C_y$-", wherein x is the minimum and y is the maximum number of carbon atoms in the substituent. Thus, for example, "$C_{1-4}$alkyl" or "$C_1$-$C_4$-alkyl" refers to an alkyl substituent containing from 1 to 4 carbon atoms.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Polymers and Hydrogels

Hydrogels are frequently utilized as three-dimensional matrices for the culture and regeneration of soft tissues, but one challenge with existing hydrogels is that, though the natural extracellular matrix of tissues may be ordered, there are few biocompatible ways to incorporate anisotropy within hydrogels. Liquid crystalline polymers are well-suited for this due to their combination of molecular ordering and polymer elasticity, however the hydrophobic nature of liquid crystalline monomers has hindered their polymerization into hydrogels under cytocompatible conditions. The present disclosure provides polymers, as well as main-chain liquid crystalline (LC) hydrogels, which may be prepared, for example by crosslinking the polymers described herein.

In one aspect, provided is a polymer of formula (I),

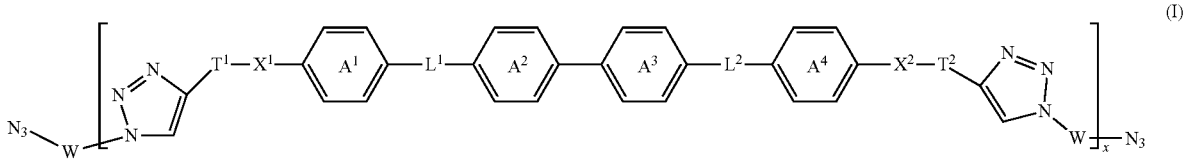

(I)

wherein $A^1$, $A^2$, $A^3$, and $A^4$ are each independently a phenyl optionally substituted with 1, 2, 3, or 4 $R^a$;

$L^1$, $L^2$, $X^1$, and $X^2$ are each independently O, NH, C(O), C(O)O, C(O)NH, or OC(O)NH;

$T^1$ and $T^2$ are each independently $C_{1-6}$alkylene;

W is $W^0$-L; wherein $W^0$ is selected from the group consisting of a polyether, a polyester, a polyamide, a polysiloxane, a polyurethane, and a combination thereof; and wherein L is a bond or —S—S—;

$R^a$ at each occurrence is independently —$NH_2$, —OH, —COOH, —CHO, halogen, cyano, —Oalkyl, —NHalkyl, —N(alkyl)$_2$, —C(O)alkyl, —C(O)Oalkyl, —OC(O)alkyl, —C(O)NHalkyl, —NHC(O)alkyl, or an alkyl optionally substituted with —$NH_2$, —OH, —COOH, or —CHO; and x is 1 to 100.

In some embodiments of formula (I), $A^1$ and $A^4$ are phenyl. In some embodiments, $A^2$ and $A^3$ are phenyl of formula (I). In some embodiments, $A^1$ $A^2$, $A^3$, and $A^4$ are phenyl.

In some embodiments of formula (I), $L^1$ and $L^2$ are C(O)O.

In some embodiments of formula (I), $X^1$ and $X^2$ are O.

In some embodiments of formula (I), $T^1$ and $T^2$ are —$CH_2CH_2CH_2$—, —$CH_2CH_2CH_2CH_2$—, or —$CH_2CH_2CH_2CH_2CH_2$—. In some embodiments of formula (I), $T^1$ and $T^2$ are —$CH_2CH_2CH_2$—.

In some embodiments of formula (I), L is a bond. In some embodiments of formula (I), L is a bond and $W^0$ is polyether, such as polyethylene oxide (PEO), polypropylene oxide, or polytetramethylene glycol. In some embodiments of formula (I), L is a bond and $W^0$ is polyethylene oxide. For example, W may be —$(CH_2CH_2O)_n$—, wherein n is 3-100, such as 3-50 or 15-25.

In some embodiments of formula (I), L is —S—S—. In some embodiments of formula (I), L is —S—S— and $W^0$ is polyether, such as polyethylene oxide (PEO), polypropylene oxide, or polytetramethylene glycol. In some embodiments of formula (I), L is —S—S— and $W^0$ is polyethylene oxide. For example, W may be —$(CH_2CH_2O)_n$—S—S—, wherein n is 3-100, such as 3-50 or 15-25.

In some embodiments of formula (I), $R^a$ at each occurrence is independently an alkyl optionally substituted with —$NH_2$, —OH, —COOH, or —CHO. In some embodiments of formula (I), $R^a$ is an unsubstituted alkyl, such as a $C_{1-4}$alkyl. In some embodiments of formula (I), $R^a$ is an alkyl substituted with —$NH_2$, —OH, —COOH, or —CHO. For example, $R^a$ at each occurrence may be independently $C_{1-4}$alkyl, $C_{1-4}$alkylene-$NH_2$, $C_{1-4}$alkylene-OH, $C_{1-4}$alkylene-COOH, or $C_{1-4}$alkylene-CHO. In some embodiments of formula (I), $R^a$ at each occurrence is independently $C_{1-4}$alkyl, $OC_{1-4}$alkyl, halogen, or cyano.

In some embodiments, the polymer of formula (I) has a structure of formula (I-a),

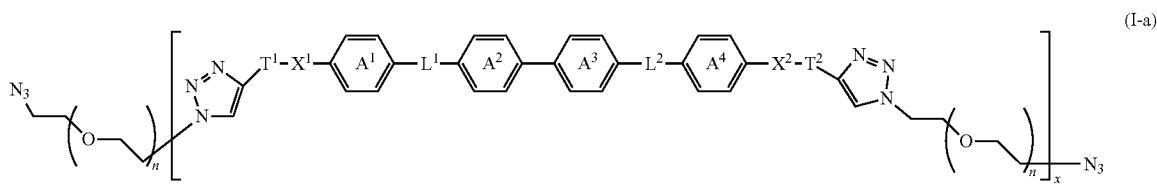

(I-a)

wherein $A^1$, $A^2$, $A^3$, $A^4$, $L^1$, $L^2$, $X^1$, $X^2$, $T^1$ $T^2$, and x are as defined in formula (I); and n is 3 to 100.

In some embodiments, the polymer of formula (I) or formula (I-a) has a structure of formula (I-a-1),

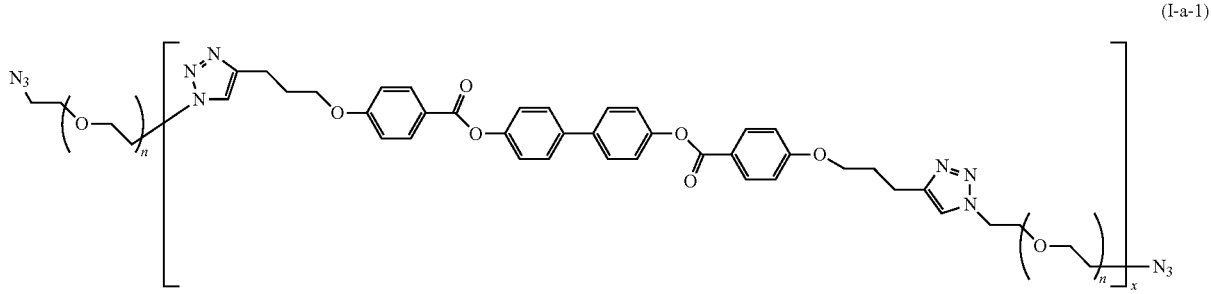

(I-a-1)

wherein x and n are as defined in formula (I-a).

In some embodiments, the polymer has a structure of formula (I), formula (I-a), or formula (I-a-1), wherein x is 1-20. In some embodiments, x is 1, 2, 3, 4, 5, 6, 7, 8, 9, or 10.

In some embodiments, the polymer has a structure of formula (I-a) or formula (I-a-1), wherein n is 3-50, such as 3-40, 3-30, 5-30, 10-30, 15-30, or 15-25. In some embodiments, n is 15-25, such as 15, 20, or 25.

In some embodiments, the polymer has a structure of formula (I), formula (I-a), or formula (I-a-1), and the polymer has a molecular weight of about 2 kDa to about 50 kDa. The molecular weight of the polymer may be about 2 kDa to about 40 kDa, about 2 kDa to about 30 kDa, or about 2 kDa to about 20 kDa. In some embodiments, the polymer has a molecular weight of about 2 kDa to about 20 kDa The polymer of formula (I) may be crosslinked by reacting with a crosslinker to form a crosslinked polymer. In another aspect, the present disclosure provides a method of preparing a crosslinked polymer, comprising reacting a polymer of formula (I) with a crosslinker, thereby forming a crosslinked polymer. In another aspect, the present disclosure provides a crosslinked polymer produced by crosslinking the polymer as described herein. In some embodiments, the polymer of formula (I), formula (I-a), or formula (I-a-1) is crosslinked through a reaction between the azide group ($N_3$) of the polymer with a reactive group of the crosslinker. The crosslinker may have 3, 4, 5, or 6 such reactive groups. In some embodiments, the reactive group of the crosslinker is a carbon-carbon double bond (C=C). In some embodiments, the crosslinker is a dibenzocyclooctyne (DBCO) derivative, such as a tetrafunctional dibenzocyclooctyne-terminated poly(ethylene oxide) (PEO) crosslinker.

In some embodiments, the polymer as described herein may be crosslinked in an aqueous medium, such as water or an aqueous buffer.

In some embodiments, the polymer as described herein may be crosslinked to form a three-dimensional polymeric network. In particular embodiments, the polymer as described herein may be crosslinked to form a three-dimensional hydrogel.

In another aspect, the present disclosure provides a crosslinked polymer comprising a moiety of formula (II), —N(alkyl)$_2$, —C(O)alkyl, —C(O)Oalkyl, —OC(O)alkyl, —C(O)NHalkyl, —NHC(O)alkyl, or an alkyl optionally substituted with —NH$_2$, —OH, —COOH, or —CHO;

x is 1 to 100; and at least one terminal indicated by 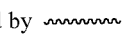 is attached to a crosslinker.

In some embodiments of formula (II), $A^1$ and $A^4$ are phenyl. In some embodiments, $A^2$ and $A^3$ are phenyl of formula (II). In some embodiments, $A^1$ $A^2$, $A^3$, and $A^4$ are phenyl.

In some embodiments of formula (II), $L^1$ and $L^2$ are C(O)O.

In some embodiments of formula (II), $X^1$ and $X^2$ are O.

In some embodiments of formula (II), $T^1$ and $T^2$ are —CH$_2$CH$_2$CH$_2$—, —CH$_2$CH$_2$CH$_2$CH$_2$—, or —CH$_2$CH$_2$CH$_2$CH$_2$CH$_2$—. In some embodiments of formula (II), $T^1$ and $T^2$ are —CH$_2$CH$_2$CH$_2$—.

In some embodiments of formula (II), L is a bond. In some embodiments of formula (II), L is a bond and $W^0$ is polyether, such as polyethylene oxide (PEO), polypropylene oxide, or polytetramethylene glycol. In some embodiments of formula (II), L is a bond and $W^0$ is polyethylene oxide. For example, W may be —(CH$_2$CH$_2$O)$_n$—, wherein n is 15-25, such as 15, 20, or 25.

In some embodiments of formula (II), L is —S—S—. In some embodiments of formula (II), L is —S—S— and $W^0$ is polyether, such as polyethylene oxide (PEO), polypropylene oxide, or polytetramethylene glycol. In some embodiments of formula (II), L is —S—S— and $W^0$ is polyethylene oxide. For example, W may be —(CH$_2$CH$_2$O)$_n$—S—S—, wherein n is 15-25, such as 15, 20, or 25.

In some embodiments of formula (II), $R^a$ at each occurrence is independently an alkyl optionally substituted with —NH$_2$, —OH, —COOH, or —CHO. In some embodiments of formula (II), $R^a$ is an unsubstituted alkyl, such as a C$_{1-4}$alkyl. In some embodiments of formula (II), $R^a$ is an alkyl substituted with —NH$_2$, —OH, —COOH, or —CHO. For example, $R^a$ at each occurrence may be independently C$_{1-4}$alkyl, C$_{1-4}$alkylene-NH$_2$, C$_{1-4}$alkylene-OH, C$_{1-4}$alkylene-COOH, or C$_{1-4}$alkylene-CHO. In some embodiments of formula (II), $R^a$ at each occurrence is independently C$_{1-4}$alkyl, OC$_{1-4}$alkyl, halogen, or cyano.

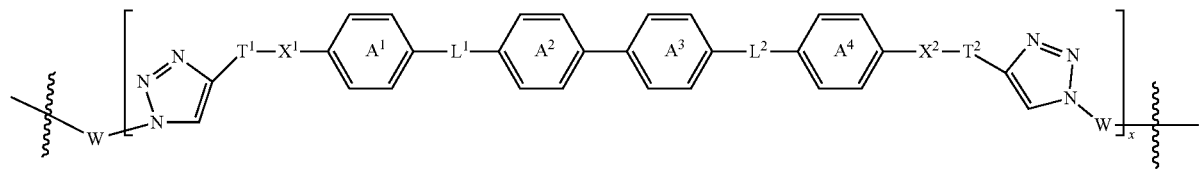

(II)

wherein $A^1$, $A^2$, $A^3$, and $A^4$ are each independently a phenyl optionally substituted with 1, 2, 3, or 4 $R^a$;

$L^1$, $L^2$, $X^1$, and $X^2$ are each independently O, NH, C(O), C(O)O, C(O)NH, or OC(O)NH;

$T^1$ and $T^2$ are each independently C$_{1-6}$alkylene;

W is $W^0$-L; wherein $W^0$ is selected from the group consisting of a polyether, a polyester, a polyamide, a polysiloxane, a polyurethane, and a combination thereof; and wherein L is a bond or —S—S—;

$R^a$ at each occurrence is independently —NH$_2$, —OH, —COOH, —CHO, halogen, cyano, —Oalkyl, —NHalkyl, The moiety of formula (II) is a structural component of the crosslinked polymer. A moiety of formula (II) may be attached to the crosslinker at one terminal or at both terminals.

The crosslinker may have three or more reactive groups, each of which may be attached to the moiety of formula (II) through a covalent bond. In some embodiments, the crosslinker has 3, 4, 5, or 6 reactive groups, each of which may be attached to the moiety of formula (II). In some embodiments, the crosslinker is a dibenzocyclooctyne (DBCO) derivative, such as a tetrafunctional dibenzocyclooctyne-terminated poly(ethylene oxide) (PEO) crosslinker.

In some embodiments, the moiety has a structure of formula (II-a),

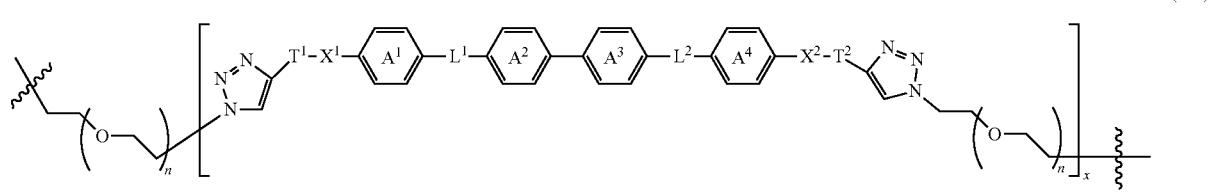

(II-a)

wherein
$A^1, A^2, A^3, A^4, L^1, L^2, X^1, X^2, T^1\ T^2$, and x are as defined in formula (II); and
n is 3 to 100.

In some embodiments, the moiety has a structure of formula (II-a-1),

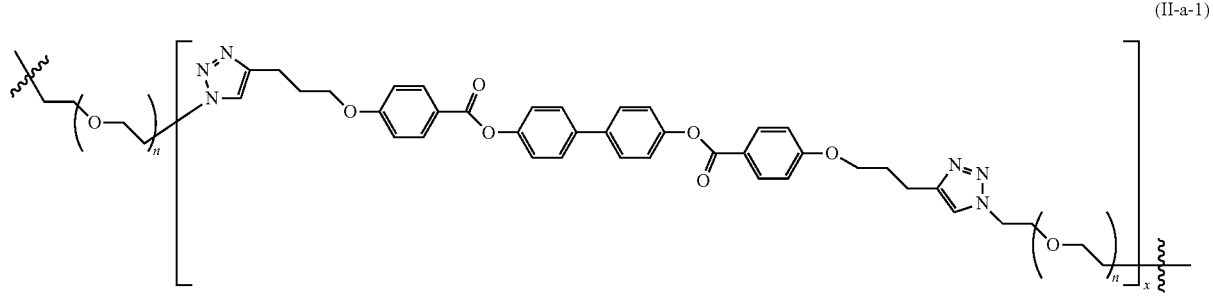

(II-a-1)

wherein x and n are as defined in formula (II-a).

In some embodiments, the moiety has a structure of formula (II), formula (II-a), or formula (II-a-1), wherein x is 1-20. In some embodiments, x is 1, 2, 3, 4, 5, 6, 7, 8, 9, or 10.

In some embodiments, the moiety has a structure of formula (II-a) or formula (II-a-1), wherein n is 3-50, such as 3-40, 3-30, 5-30, 10-30, 15-30, or 15-25. In some embodiments, n is 15-25, such as 15, 20, or 25.

In some embodiments, the moiety has a structure of formula (II), formula (II-a), or formula (II-a-1), and the moiety has a molecular weight of about 2 kDa to about 50 kDa. The molecular weight of the moiety may be about 2 kDa to about 40 kDa, about 2 kDa to about 30 kDa, or about 2 kDa to about 20 kDa. In some embodiments, the moiety has a molecular weight of about 2 kDa to about 20 kDa.

In some embodiments, the crosslinked polymer disclosed herein forms a three-dimensional polymeric network, such as a three-dimensional hydrogel. In particular embodiments, the crosslinked polymer disclosed herein may forms a main-chain liquid crystalline (LC) hydrogel in an aqueous medium, and the LC phase is able to affect mesenchymal stem cell behavior.

In some embodiments, the crosslinked polymer disclosed herein results in high gel fraction materials. In particular embodiments, the three-dimensional network formed by the crosslinked polymer disclosed herein organizes into LC phases in the dry and hydrogel states, as shown by calorimetry, thermomechanical measurement, and X-ray scattering analysis.

In particular embodiments, the present disclosure provides synthetic thermotropic LC polymers that are water soluble and able to be subsequently crosslinked using strain-promoted alkyne-azide cycloaddition (SPAAC). This approach permits the polymerization of a hydrophobic mesogen with a hydrophilic chain extender in a polar organic solvent to generate a water-soluble LC polymer, which may be purified and crosslinked under cytocompatible conditions in aqueous media. The present disclosure directly incorporates a calamitic (rod-like) mesogen into the backbone of the hydrogel network, which is a significant departure from previous efforts (e.g., using LC solvents to swell polymers into a gel, polymerizing disc-like molecules to generate LC order within a hydrogel, or generating gels that form lyotropic LC phases through the interaction of various molecules). The present disclosure thus directly couples mesogen phase behavior to polymer chain behavior, thereby affording potential to alter chain viscoelasticity and to impart anisotropic and stimuli-responsive properties to the hydrogels.

3. Method

The crosslinked polymers described herein may be used as an anisotropic material for controlling mechanical properties and transport of substances. For example, the present crosslinked polymers may be used as an actuating material suitable for a variety of applications, including but not limited to robotics and valves, or as a substrate for tissue culture.

In one aspect, the present disclosure provides a method of culturing a plurality of cells, comprising
crosslinking a polymer of formula (I) as described herein by a crosslinker in a medium in which the cells are dispensed, thereby forming a three-dimensional network of the crosslinked polymer and encapsulating the cells in the three-dimensional network; and
culturing the encapsulated cells.

In some embodiments, the crosslinker is a dibenzocyclooctyne (DBCO) derivative, such as a tetrafunctional dibenzocyclooctyne-terminated poly(ethylene oxide) (PEO) crosslinker.-

In some embodiments, wherein the crosslinking comprises mixing the crosslinker and the cells in the medium to form a mixture; and adding the polymer to the mixture.

The plurality of cells may comprise a human cell or an animal cell. Suitable human or animal cells may include, but are not limited to, blood cells, muscle cells, heart cells, liver cells, kidney cells, skin cells, neurons, stem cells, or a combination thereof. The stem cells may include mesenchymal stem cells, neural stem cells, embryonic stem cells, or a combination thereof. In some embodiments, the plurality of cells may comprise a human mesenchymal stem cell (hMSCs). Clinical trials suggested the role of hMSCs in the secretion of paracrine signals that positively influence local tissue repair and regeneration. As a primary cell, hMSCs provide a biological platform for probing the roles of extracellular structure and organization on stem cell fate. Thus, the present method may be used to modulate cell and protein function within 3D tissue constructs in biological studies.

In particular embodiments, hMSCs are cultured within the hydrogels according the present method, and the cell show excellent viability, and hMSC proliferation proceeds at a faster rate in LC hydrogels compared to non-liquid crystalline hydrogels. The present method thus provides a synthetic approach for calamitic liquid crystalline hydrogels, which may support the encapsulation and culture of human stem cells and enable applications as anisotropic and responsive substrates for tissue engineering and regenerative medicine.

The present hydrogels permit liquid crystalline order using a liquid crystalline polymer, and the polymers may be crosslinked under conditions that do not damage a cell and that support cell culture. Remarkably, the hydrogels and methods disclosed herein contain advantages when compared to the current materials and approaches.

Current methods to incorporate anisotropy within a hydrogel without using liquid crystalline materials include: (a) applying mechanical forces (compression/stretching) to gel materials to align polymer chains; (b) using 3D printing to shear viscous materials to align polymer chains; (c) using crosslinking chemistries that work with photo patterning so that regions with more/less of crosslinking can be prepared, which generates patterns of stiffness and therefore anisotropic mechanical properties; (d) combining polymers with particles that can be aligned in an by shearing or the application of an electric or magnetic field to make an anisotropic gel; and (e) combining polymers with particles or other substances that can later be dissolved or sublimed (e.g., directional freezing methods to form ice crystals that are subsequently sublimed out of the network to leave aligned channels within a network).

Compared to the above methods, the LC hydrogel described herein does not need mechanical, electrical, or magnetic forces to form an ordered state and therefore has the potential to form an ordered phase. In particular, when used as cell culture substrate, the present LC hydrogel may form an ordered phase while cells are present and without damaging the cells.

Current methods to incorporate anisotropy within a hydrogel using liquid crystalline materials include: (a) lyotropic liquid crystalline hydrogels, in which molecules (usually amphiphilic molecules) self-assemble to form liquid crystalline phases spontaneously in water; however, these materials do not couple LC order to polymer phase behavior; (b) swelling of liquid crystalline polymer with solvents; however, none of these swollen networks have sufficient degree of swelling, nor can the existing materials be polymerized in the presence of cells (such that encapsulating the cells in the network and providing nutrient/waste exchange would be very difficult, if not impossible); and (c) chromonic liquid crystalline polymers; however, such material uses a different type of liquid crystal. In comparison, the polymers and hydrogels as disclosed herein may be liquid crystalline without solvent, and may more strongly couple molecular order to polymer chain behavior.

4. Examples

Materials and Methods 5-chloro-1-pentyne (98%), 4-hydrozybenzoic acid (99%), 3-dicyclohexylcarbodiimide (99%), 4-(dimethylamino)pyridine (99%), potassium hydroxide (≥90%), 4,4-dihydroxybiphenyl (97%), copper (I) bromide (Cu(I)Br, 98%), N,N-dimethylformamide (DMF, ≥99.9%), anhydrous dichloromethane (DCM, 99.8%), deuterated chloroform ($CDCl_3$, 99.8 atom % D), and ethylenediaminetetraacetic acid (EDTA, ≥98.5%) were purchased from Millipore Sigma (Burlington, Mass.). Hydrochloric acid (ACS Plus grade), dichloromethane (DCM, 99.9%), methanol ($CH_3OH$, 99.9%), hexanes (Certified), 2-propanol (99.9%), glacial acetic acid (Certified ACS Plus), acetonitrile (≥99.5%), ethyl acetate (99.8%), anhydrous magnesium sulfate ($MgSO_4$, Certified), live/dead cell stains (calcein AM and ethidium homodimer-1), Dulbecco's modified eagle medium (DMEM), alamarBlue cell viability reagent, fetal bovine serum (FBS, qualified), phosphate-buffered saline (PBS, 1×, sterile), and Antibiotic-Antimycotic (anti-anti, 100×) were purchased from Fisher Scientific (Waltham, Mass.). A tetrafunctional dibenzocyclooctyne-terminated poly(ethylene oxide) (PEO) crosslinker with $M_w$~5000 Da (4-arm PEO-DBCO) and PEO diazide chain extenders with $M_w$~1000 Da (PEO20-diazide) and $M_w$~3400 Da (PEO75-diazide) were purchased from Creative PEGWorks (Chapel Hill, N.C.). Human mesenchymal stem cells (hMSCs) derived from adipose (Passage 1) were purchased from Lonza (Walkersville, Md.) and were expanded until use at Passage 6. Ultrapure water ($dH_2O$, 18 MOhm·cm) was obtained from an in-house system. 4,4-dihydroxybiphenyl was purified by recrystallization in acetonitrile (2 g/100 mL) to yield white crystals. Cu(I)Br was washed by glacial acetic acid followed by 2-propanol. DMF was sparged with nitrogen for 2-3 h prior to the experiments. All the other reagents were used as received.

Chemical structures were characterized using proton nuclear magnetic resonance spectroscopy ($^1H$ NMR) on a Bruker ADVANCE 300 MHz NMR running Topspin 2.1 (Billerica, Mass.). $^1H$ NMR data were analyzed using MestReNova version 9.0 from Mesrelab Research S.L. (Escondido, Calif.). Thermal properties of monomers and polymers were characterized using differential scanning calorimetry (DSC) (Q20/Q100 with Q Series Software (version 5.3.0) and Universal Analysis (version 4.5A) from TA Instruments, New Castle, Del.). The samples were cooled to −80° C. at 10° C. $min^{-1}$, held for 2 min, heated to the isotropic phase at 10° C./min, held for 2 min, cooled again to −80° C. at 10° C. $min^{-1}$, and held for 2 min. The cycle was repeated, and the second cycle was used to investigate thermal properties of samples, except for the 1,1'-biphenyl (4,4'-bis(4-pentyloxybenzoate)) (5yHBP) monomers where the first heating cycle was used. Polarized optical microscopy (POM) images of monomers and polymers were collected using a Olympus BX50 Microscope (Center Valley, Pa.) equipped with a PAXcam (Villa Park, Ill.) while the samples were heated from 20° C. to 220° C. at 10° C. $min^{-1}$ using a thermal stage from Instec Inc. (Boulder, Colo.). Storage modulus and loss modulus were measured as a function of temperature using dynamic mechanical analysis (DMA) (Q800 with Thermal Advantage software (version 1.1A) and Universal Analysis software (version 4.5A) from TA Instruments, New Castle, Del.). Films of LCNs (typical size: 10 mm l×2.0 mm w×0.2 mm t) were mounted in the tension film clamp, and the samples were oscillated at a prescribed amplitude (10 μm) and frequency (1 Hz) while heating from −70° C. to 120° C. at 3° C. min$^{-1}$. Two-way shape memory was also performed on a dynamic mechanical analyzer using controlled force mode. The networks were mounted in the tension film clamp and stretched in the isotropic phase at 100° C. until reaching a specified stress. The networks were then cooled to the liquid crystalline phase at 3° C. min$^{-1}$ until reaching −70° C. before heating again at 3° C. min$^{-1}$ under the same load. The procedure was then repeated using a different stress.

Wide-angle X-ray scattering (WAXS) experiments were performed on an Xcalibur PX Ultra, and data was collected and analyzed using CrysAlisPro (Version 1.171) from Oxford Diffraction (Concord, Mass.). Small-angle X-ray scattering (SAXS) experiments were performed on a Bruker NanoStar using Cu Kα radiation (λ=1.5405 Å). Small Angle X-ray Scattering System software (V4.1.45) from Bruker (Billerica, Mass.) was used to collect and analyze SAXS data. For SAXS measured at different temperatures, the measurements were run by heating from 25° C. to 90° C. and holding isothermally at the temperature of interest for 10 min prior to starting the exposure. To quantify gelation kinetics, an AR-G2 rheometer running TRIOS software (version 4.5.1 from TA Instruments, New Castle, Del.) equipped with 8 mm parallel plate was used to shear samples at 15° C. with oscillation frequency of 10 rad/s, gap of 220 μm, and strain amplitude of 10%. Modulus of hydrogels as a function of temperature was also measured using AR-G2 rheometer with 8 mm parallel plate by heating samples from 15° C. to 65° C. at 1° C. min$^{-1}$ with frequency of 1 rad/s, gap of 220 μm, and strain amplitude of 5%. A solvent trap filled with DI water was used to maintain hydration during the rheology experiments.

For statistical analysis, two-way analysis of a variance (ANOVA) with a Holm-Sidak test was used to evaluate the differences of the means from the proliferation data. The statistical testing was completed using Origin Pro 8.1 from OriginLab Corporation (Northampton, Mass.). A statistically significant value was determined if the p-value was less than 0.05.

Unless indicated otherwise, the following formula and abbreviations are used herein. Anti-Anti: Antibiotic-Antimycotic; $CH_3OH$: methanol; $CO_2$: carbon dioxide; CuBr: copper bromide; $CDCl_3$: deuterated chloroform; DCM: dichloromethane; ΔH: latent heat of a transition; DBCO: dibenzocyclooctyne; $dH_2O$: ultrapure water; DMA: dynamic mechanical analysis; DMF: dimethylformamide; DSC: differential scanning calorimetry; DMEM: Dulbecco's modified eagle medium; EDTA: ethylenediaminetetraacetic acid; FA: focal adhesions; FBS: fetal bovine serum; $^1$H NMR: proton nuclear magnetic resonance spectroscopy; hMSC: human mesenchymal stem cell; LC: liquid crystalline; LCP: liquid crystal polymers; LCN: liquid crystalline network; $MgSO_4$: magnesium sulfate; PBS: phosphate-buffered saline; PEO: poly(ethylene oxide); POM: polarized light optical microscopy; SAXS: small-angle X-ray scattering; SPAAC: strain-promoted alkyne-azide cycloaddition; WAXS: wide-angle X-ray scattering; 2D: two-dimensional; 3D: three-dimensional.

Example 1. Synthesis and Characterization of Polymer Networks

Synthesis of 1,1'-biphenyl(4,4'-bis(4-pentyloxybenzoate)) (5yHBP)

5yHBP was synthesized as shown in Scheme 1 using 4,4-dihydroxybiphenyl. 5yHBP was purified by recrystallizing from a mixture of ethyl acetate and 2-propanol (5/1, volume ratio). The yield of 5yHBP was about 63%. Proton nuclear magnetic resonance spectroscopy ($^1$H NMR) in $CDCl_3$ resulted in the following chemical shifts (δ) for 5yHBP in ppm: 8.17 (4H, m), 7.63 (4H, m), 7.28 (4H, m), 7.00 (4H, m), 4.18 (4H, t), 2.44 (4H, m), 2.04 (6H, m).

Scheme 1

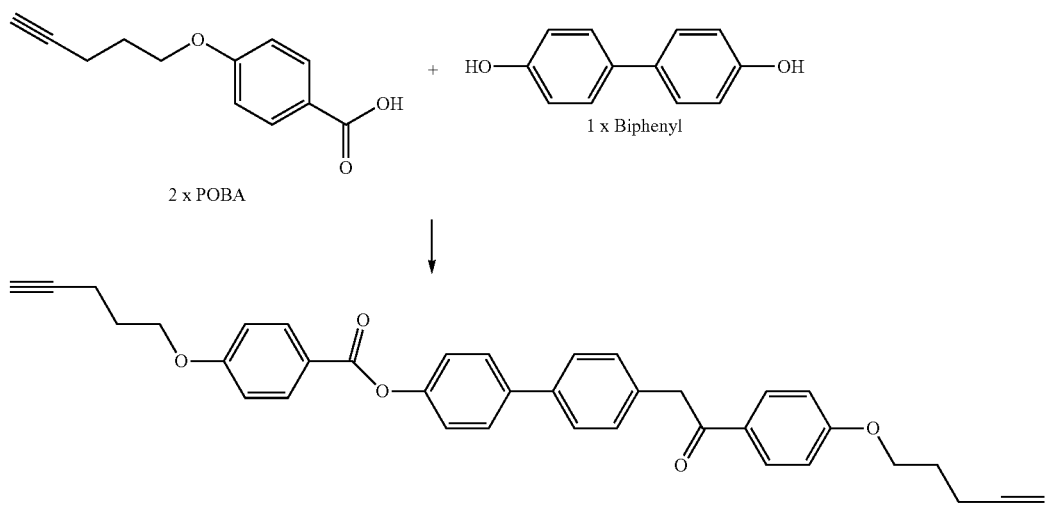

Scheme of 5yHBP mesogen synthesis. Conditions: 12.9 mmol biphenyl, 28.4 mmol POBA, 29.2 mmol DCC, and 2.62 mmol DMAP in anhydrous DMAP in anhydrouis DCM (60.3 ml). React at room temperature with magnetic stirring for 72 h.

Synthesis of Linear 5yHBP-PEO20 Polymers

5yHBP (71.5 mg, 0.128 mmol) was weighed into a 25 mL Schlenk flask and purged with nitrogen gas for 3 min.

Anhydrous DCM (2 mL) was added into the flask to dissolve the mesogen, followed by adding PEO20-diazide (141 mg, 0.141 mmol) to the flask. Cu(I)Br (20.0 mg, 0.0140 mmol) was dissolved in 0.4 mL deoxygenated DMF, and the catalyst solution was injected into the flask after the mesogen and PEO20-diazide were completely dissolved. The reacting mixture was stirred at 55° C. for 72 h. The synthesis of 5yHBP-PEO20 polymers was shown in Scheme 2. The crude product solution was diluted with DCM (100 mL) and then washed with 0.1M EDTA(aq) (100 mL×3) and $dH_2O$ (100 mL×1). The aqueous phase was discarded and the organic phase was dried over anhydrous $MgSO_4$, and the solvent was removed using rotary evaporation to yield a white solid. The naming convention for the linear polymers is as follows: 5yHBP-PEO20-XX, where XX denotes the molecular weight of the polymer in kilodaltons (kDa) that was determined using $^1H$ NMR. $^1H$ NMR (300 MHz) in $CDCl_3$ resulted in the following chemical shifts for 5yHBP-PEO20-4.1 polymers in ppm: 8.16 (8H, m), 7.63 (8H, m), 7.54 (4H, s), 7.28 (8H, m), 7.00 (8H, m), 4.51 (8H, m), 4.12 (8H, m), 3.86 (8H, t) 3.64 (244H, m), 3.39 (4H, t), 2.91 (8H, m), 2.24 (8H, m). To compare the properties of 5yHBP-PEO20 polymers with different molecular weight, 5yHBP-PEO20-7.2k and 5yHBP-PEO-10.3 were synthesized using the same procedure but with different amounts of PEO20-diazide (138 mg for 5yHBP-PEO20-7.2k and 135 mg for 5yHBP-PEO-10.3)

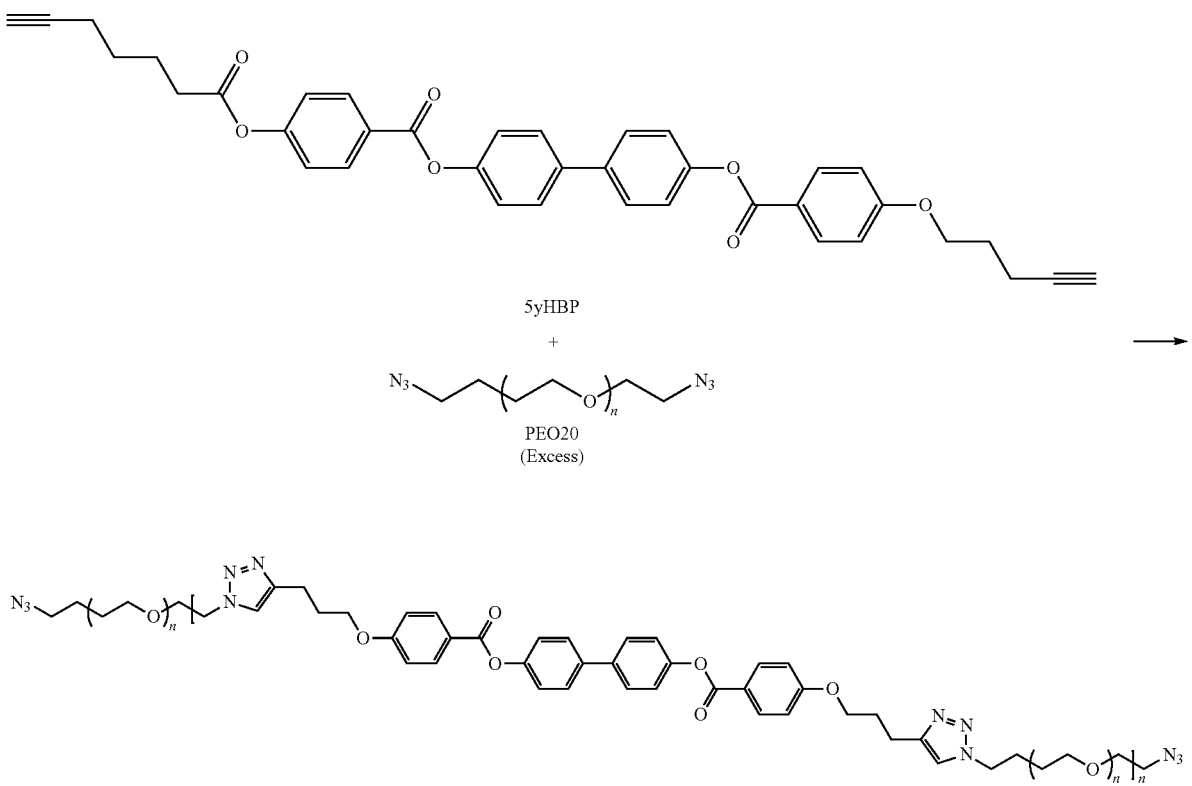

Synthesis of 5YHBP-peo20 liquid crystalline polymers using alkyne-azide cycloaddition, where PEO20 was in excess relative to mesogen (as described in Section 2.4). Conditions: Catalyst (10 mmol/mmol 5y HBP), DMF/DCM, 50° C., 72 h.

Purity and molecular weight of the prepolymers were determined by using $^1H$ NMR as follows.

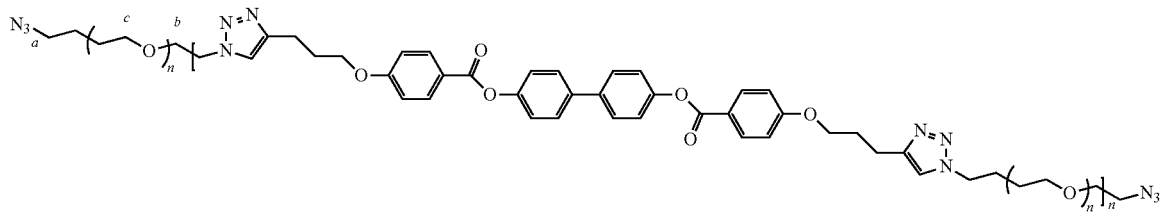

Step 1. The protons (labeled "a") that are attached on the carbon alpha to the azide occur at 3.39 ppm. There should be four of these protons for each polymer because the polymer is terminated on both ends with an azide. This peak was thus normalized to four protons.

Step 2. Within the PEG oligomer, there are protons that are located at 4.51 ppm. These protons (labeled "b") are attached to the carbon beta to the triazole. For each reaction between an alkyne and azide, one triazole linkage results. There should be two protons at 4.51 ppm for each triazole linkage, therefore dividing the integrated area by two allows calculation of the number of triazole linkages present in the polymer.

Step 3. It is known that there are no free alkyne groups within the sample (this peak was not observed in the polymer). Therefore, any mesogen present must be terminated with a triazole linkage on both ends of the molecule. By dividing the number of triazole linkages (determined in Step 2) by 2, the number of mesogens in the polymer were calculated.

Step 4. The number of PEG oligomers in the polymer should be one greater than the number of mesogens. This is because both ends of the polymer terminate in PEG (e.g., the polymer takes the form of $(A-B)_n-A$). The number of PEG oligomers in the polymer can therefore be calculated by adding one to the number of mesogens determined in Step 3.

Step 5. Methylene protons within the PEG repeat occur at 3.64 ppm (labeled "c" in the figure below). The number of expected protons from the peak integration can be calculated by multiplying the number of PEG oligomers in the polymer (determined in Step 4) by the number of methylene protons in the PEG oligomer (80 protons). This number should be equal to the area associated with the protons at 3.64 ppm. If the actual area is different than this number, it means that either: 1) the polymer is not terminated with PEG (not likely because there would have been a signal from the alkyne groups, which was not observed), or 2) there is free PEG in the system. The balance worked, however, so it was concluded that polymers are terminated with azide groups and that there is no unreacted PEG in the purified polymers.

Step 6. The molecular weight was then calculated knowing the number of PEG oligomers (from Step 4) and mesogen (from Step 3) in the polymer. This is a number averaged molecular weight.

Synthesis of 5yHBP-PEO20 Networks Using Copper-Free Click Chemistry

Linear 5yHBP-PEO20-4.1 polymers (10.0 mg, 0.00244 mmol) and 4-arm PEO-DBCO (6.10 mg, 0.00122 mmol) were dissolved in 90.0 µL $dH_2O$ water and 40.8 µL $dH_2O$ water, respectively. The two solutions were mixed at room temperature, resulting in gelation (Scheme 2; full structure shown in FIG. 1). The naming convention for the crosslinked networks is as follows: N-5yHBP-PEO20-XX, where XX denotes the molecular weight of the polymer in kilodaltons (kDa). As a comparison to LC networks, PEO75-diazide was selected as a non-liquid crystalline linear polymer for crosslinking because it has similar mass content of PEO as 5yHBP-PEO20-4.1. The non-liquid crystalline network N-PEO75 was synthesized using the same method, where PEO75-azide (8.30 mg, 0.00244 mmol) in 47.0 µL $dH_2O$ was used instead of the LC polymer solution.

To characterize the crosslinking reaction, each network was washed three times for 2 h each using DMF before washing with DI water three times for 2 h each. This process removed any linear polymers trapped in the network prior to characterization to ensure that data collected arises from the chemically crosslinked networks. The dry mass of networks was measured before and after washing, and gel fraction was calculated by dividing post-extraction mass by pre-extraction mass. Gel fractions of the network were always higher than 75%, indicating successful crosslinking of polymers and their incorporation into the network.

Scheme 3

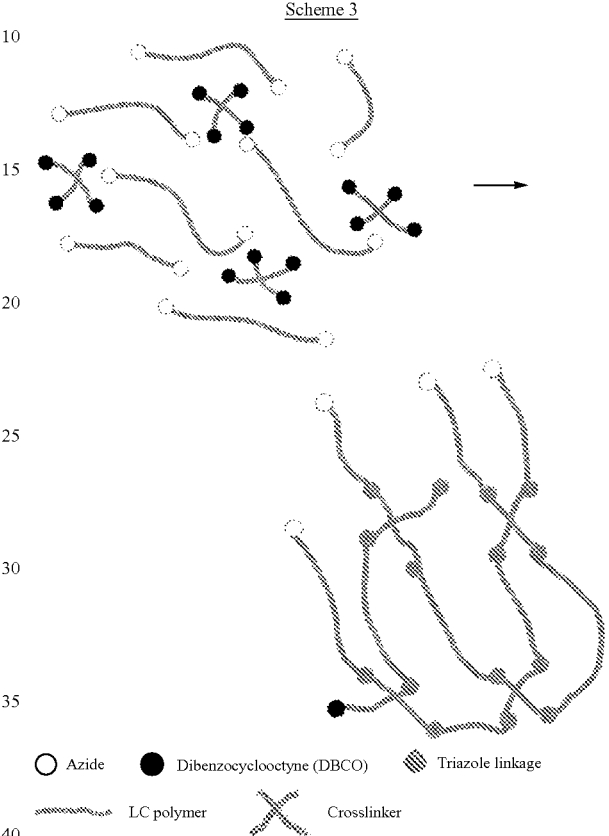

○ Azide    ● Dibenzocyclooctyne (DBCO)    ▨ Triazole linkage

∽∽∽∽ LC polymer    ✕ Crosslinker

Scheme of crosslinking 5yHBP-PEO20-4.1 in water using copper-free strain promoted alkyne-azide cycloaddition (SPAAC).

Phase Behavior of 5yHBP Monomers

Figure 2A:
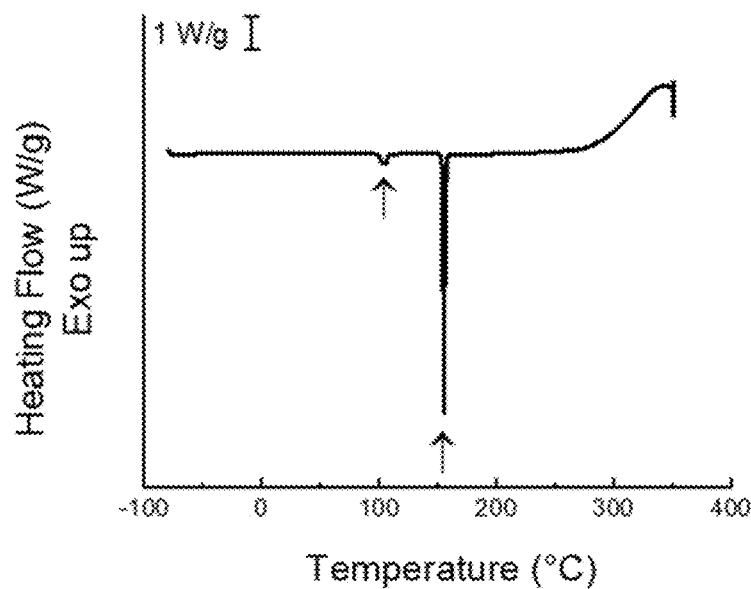
FIGS. 2A and 2B show the thermal properties of the 5yHBP mesogen.
Figure 2B:
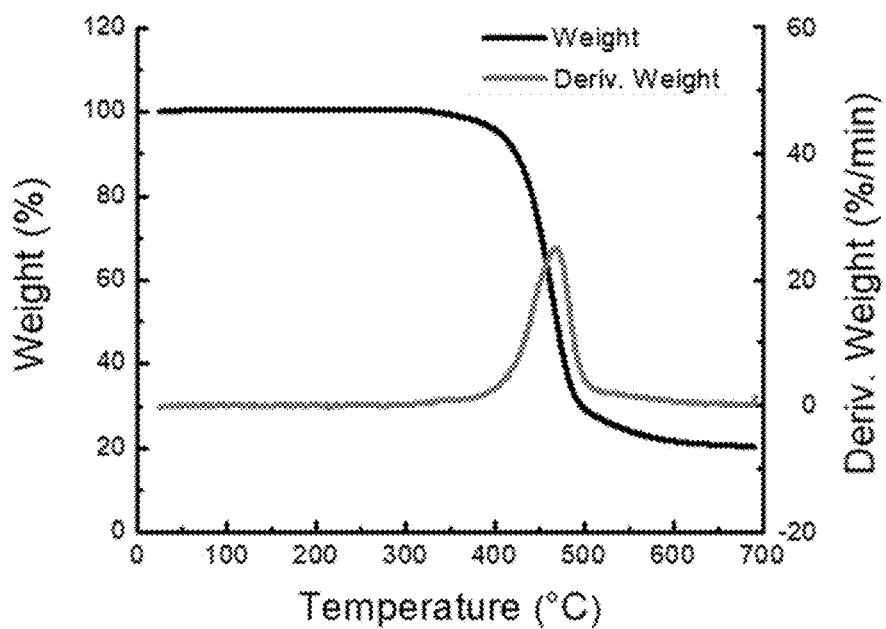
Figure 3A:
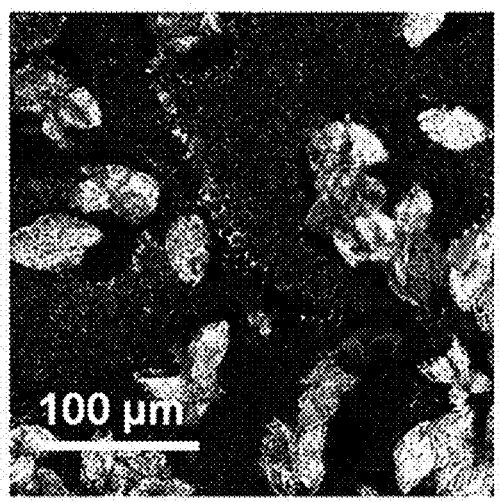
FIGS. 3A, 3B, and 3C show the Polarized optical microscopy (POM) images of 5yHBP heated from the crystal state to the liquid crystalline phase at 10° C. min⁻¹ at the following temperatures: 70° C.
Figure 3B:
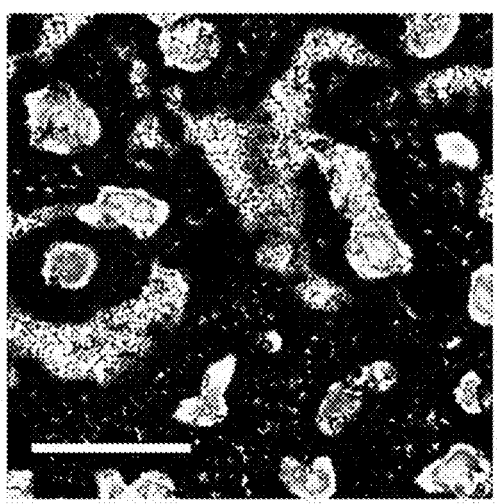
Figure 3C:
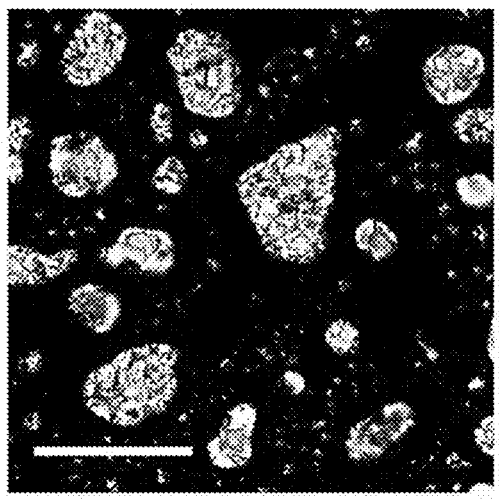

The thermal transitions of 5yHBP, the liquid crystalline monomer used in this work, were characterized by differential scanning calorimetry (DSC) and polarized optical microscopy (POM). The first heating trace of DSC measured at 10° C. $min^{-1}$ is shown in FIGS. 2A and 2B, and displays an endotherm at 105.4° C. (12.7 J $g^{-1}$), a larger endotherm at 154.1° C. (74.8 J $g^{-1}$), and finally an increase in the heat flow trace above 250° C. This increase in heat flow at high temperature may be due to the self-reaction of alkynes or degradation of the monomer occurring above 250° C. Either of these events could result in structural changes to the mesogen that would prevent isotropization from being detected on subsequent cycles in the DSC traces. Thermogravimetric analysis of 5yHBP mesogens (FIGS. 2A and 2B) indicates a decomposition starting around 420° C., thus the increase observed in the DSC heat flow is attributed to the self-reaction of alkyne groups. This behavior is consistent with the literature, where it has been observed that isotropization temperature of biphenyl liquid crystals can exceed their decomposition temperature and thus prevent the detection of the LC to isotropic phase transition using DSC. POM images acquired from the first heating of 5yHBP from 20° C. to 220° C. at 10° C. $min^{-1}$ (FIGS. 3A, 3B, and 3C) show that the birefringent crystals observed at 70° C. become threaded LC patterns upon heating and suggest that 5yHBP forms a nematic and/or smectic LC phase after its melting transition, which is consistent with mesogens having the same aromatic core.

Characterization of Linear 5yHBP-PEO20 Polymers

Without being limited to any particular theory, it was hypothesized that tuning the composition of the mesogen (to affect LC phase stability) and the molecular weight of the hydrophilic spacers would permit the generation of the water-soluble LC polymers. To identify suitable polymer compositions, data collected from a previous study and preliminary experiments were used. Previously, polymerizing a lower molecular weight PEO-diazide (244 Da) with 5yH, a mesogen whose aromatic core has a smaller aspect ratio than 5yHBP, resulted in polymers that were LC in the dry state. Those polymers were not soluble in water, therefore they were crosslinked in organic solvent before drying and hydrating in water. This approach is not suitable for cell encapsulation. Moving forward, the molecular weight of PEO-diazide was increased to ~1000 Da (this is PEO20-diazide), but polymers containing 5yH were only weakly LC in the dry state. Water soluble LC polymers thus required the polymerization of PEO20-diazide with a mesogen that formed a stronger LC phase, which necessitated the replacement of 5yH with 5yHBP in this work. Liquid crystalline polymers were successfully synthesized by reacting 5yHBP with azide-endcapped PEO (PEO20-diazide) (Scheme 2), and the resulting 5yHBP-PEO20 polymers were characterized for their molecular weight, aqueous solubility, and phase behavior. From here, the composition of the mesogen (5yHBP) and PEO (PEO20-diazide) remained fixed and the ratios of reactants were varied to obtain azide-terminated polymers of varying molecular weight (from 4.1 to 10.3 kDa). The naming convention for the linear polymers is as follows: 5yHBP-PEO20-XX, where XX denotes the molecular weight of the polymer in kilodaltons (kDa).

Figure 4A:
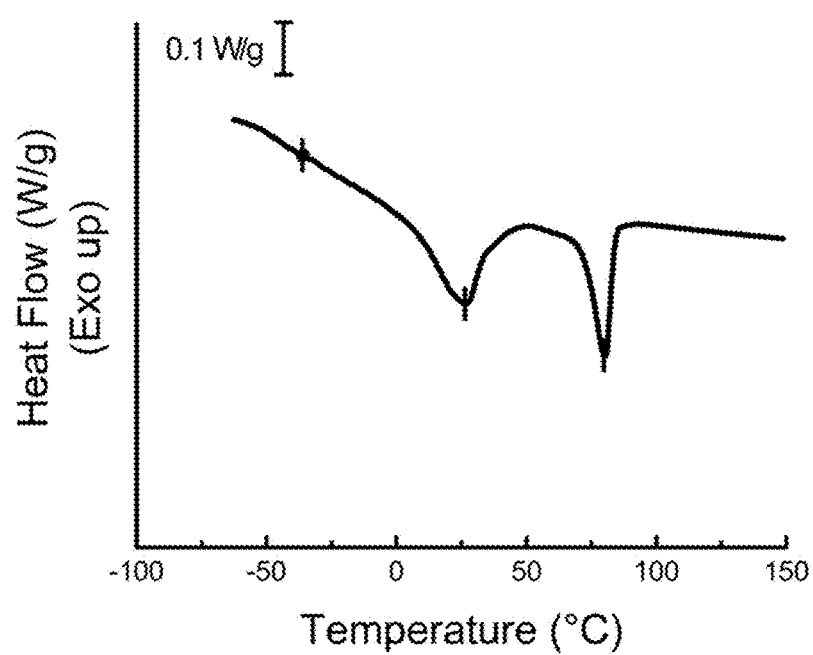
FIG. 4A shows second heating differential scanning calorimetry (DSC) trace of 5yHBP-PEO20-4.1 polymers.
Figure 4B:
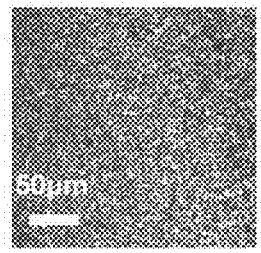
FIGS. 4B-4D show polarized optical microscopy (POM) images of 5yHBP-PEO20-4.1 polymers heated at 10° C. min⁻¹, where images were acquired at the following temperatures: 70° C.
Figure 4C:
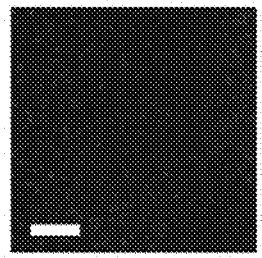
Figure 4D:
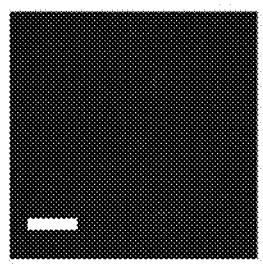
Figure 4E:
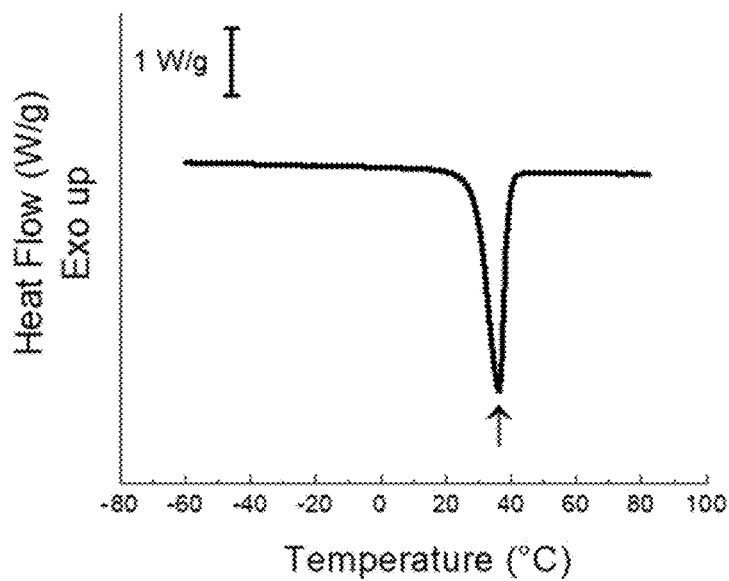
FIG. 4E shows DSC second heating trace of PEO20. Vertical arrows were added to highlight the transition.
Figure 5:
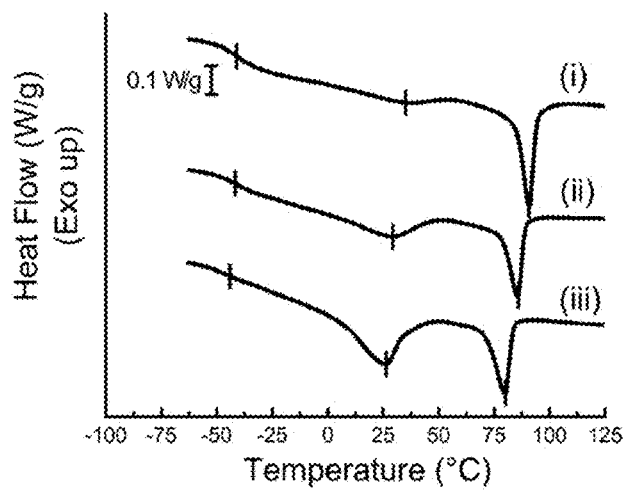
FIG. 5 shows effect of LC polymer molecular weight on the glass transition, PEO melting transition, and isotropization transition. The DSC second heating traces of (i) 5yHBP-PEO20-10.3, (ii) 5yHBP-PEO20-7.2, and (iii) 5yHBP-PEO20-4.1 are shown. Ticks are used to highlight the transitions.

The synthesis of 5yHBP-PEO20-4.1 is described in the Experimental Section, and the polymer's solubility in dH$_2$O water is about 150 mg mL$^{-1}$. Reducing the ratio of PEO20 to 5yHBP generated azide-endcapped polymers with different molecular weights (7.2 kDa and 10.3 kDa). These polymers have more hydrophobic mesogen than 5yHBP-PEO20-4.1 and were found to have lower aqueous solubility than 5yHBP-PEO20-4.1. For each composition, solubility was assessed visually by confirming a homogenous solution. The presence of structures, such as micelles, in the solutions was not studied. DSC and POM were used to determine thermal transitions of linear 5yHBP-PEO20-4.1 (FIGS. 4A-4D). The second heating trace of 5yHBP-PEO20-4.1 showed a stepwise decrease at −45.8° C., which is attributed to the glass transition, followed by two endothermic peaks at 26.8° C. (ΔH=18.4 J g$^{-1}$) and 80.6° C. (ΔH=13.3 J g$^{-1}$) (FIG. 4A). The first endothermic transition is attributed to melting of PEO, a finding that is confirmed by the melting point of PEO20 shown in FIG. 4E. The second endothermic peak is attributed to the isotropization transition of the LC polymer, which is supported by the POM images (FIGS. 4B-4D) acquired upon heating from 70° C. to 110° C. that show the disappearance of a birefringent, threaded texture after heating above 80° C. 5yHBP-PEO20 polymers with higher molecular weight (7.2 k and 10.3 k) were also synthesized by modifying ratio of 5yHBP and PEO20 in the polymerization reaction as described herein. By comparing the DSC second heating traces of these three polymers (FIG. 5), 5yHBP-PEO20-10.3 displayed the highest isotropization temperature at 90.8° C. with the largest latent heat of isotropization (ΔH=16.0 J g$^{-1}$), 5yHBP-PEO20-7.2 displayed an intermediate values (isotropization temperature at 85.7° C. and ΔH=14.3 J g$^{-1}$), and 5yHBP-PEO20-4.1 displayed the lowest isotropization temperature (80.6° C.) and the smallest latent heat of isotropization (13.3 J g$^{-1}$). These results indicate that strength of the LC organization increases as polymer molecular weight increases, a finding that is attributed to the greater mesogen content in polymers with larger molecular weights.

Thermomechanical Properties of Dry 5yHBP-PEO20 Networks

Azide-endcapped 5yHBP-PEO20 polymers were crosslinked in water via copper-free cycloaddition chemistry to generate liquid crystalline networks (Scheme 3) with gel fractions that always exceeded 75%. The naming convention for the crosslinked networks is as follows: N-5yHBP-PEO20-XX, where XX denotes the molecular weight of the polymer in kilodaltons (kDa). Because crosslinking results in the dilution of the aqueous polymer solution, we decided to focus on 5yHBP-PEO20-4.1 because this polymer is soluble at a wider range of concentrations compared to the other higher molecular weight polymers. Additionally, 5yHBP-PEO20-4.1 is more easily mixed using a micropipette, which is needed for eventual mixing with cell suspensions. DSC and dynamic mechanical analysis (DMA) were used to characterize the thermomechanical properties of N-5yHBP-PEO20-4.1. The DSC second heating trace (FIG. 6A) showed a glass transition at −36.0° C. and two endothermic peaks, the first of which was located at 20.8° C. (26.15 J g$^{-1}$) and is attributed to the melting transition of PEO. The second endothermic peak was at 79.1° C. (2.9 J g$^{-1}$) and is attributed to the isotropization transition. Comparing with the linear polymer (5yHBP-PEO20-4.1), the networks thus showed weaker LC organization (characterized by a lower isotropization temperature) and a stronger melting transition of PEO, which may be due to the larger amount of PEO in the network arising from the contributions from the PEO crosslinker. However, it is important to note that the melting of PEO in the LC network is subambient, thus the LC networks are not crystalline at or above room temperature. The DSC traces of the non-liquid crystalline network, N-PEO75, prepared to have a similar mass content of PEO show only an endotherm due to the melting transition of PEO at 39.2° C. (ΔH=67.6 J g$^{-1}$) and an exotherm due to the crystallization of PEO at 23.95° C. (ΔH=67.2 J g$^1$) (FIGS. 7A and 7B).

Figure 6A:
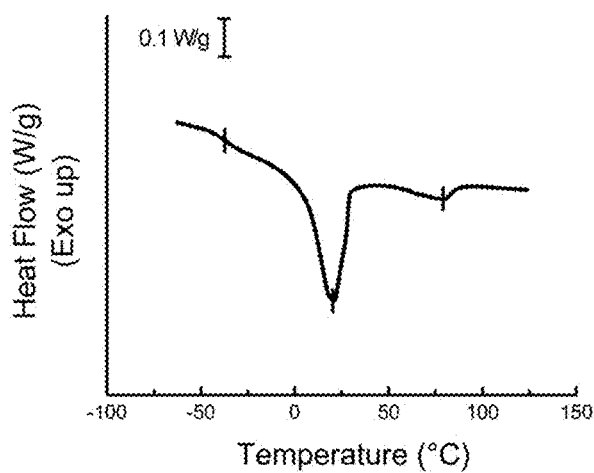
FIGS. 6A and 6B show the thermomechanical properties of dry liquid crystalline networks.
Figure 6B:
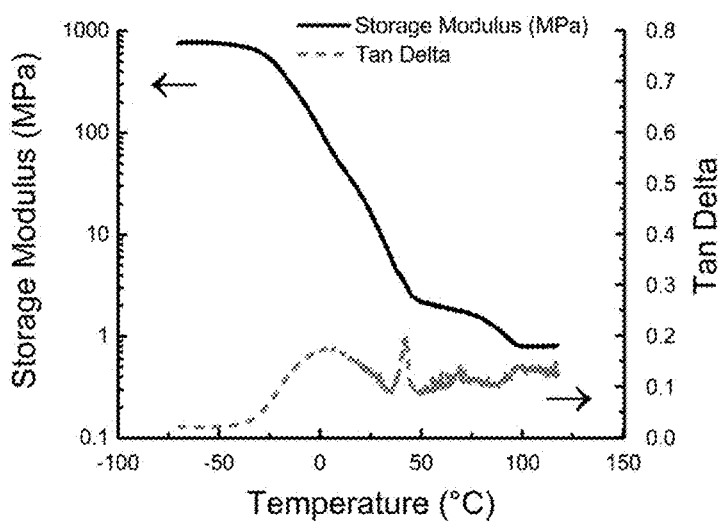

Thermomechanical testing (FIG. 6B) showed that N-5yHBP-PEO20-4.1 underwent a large stepwise decrease in storage modulus from −26.8° C. to 45.5° C. and that this is accompanied by two peaks located in the tan delta trace. The onsets of these stepwise transitions are difficult to quantify, but are in better agreement with the calorimetry data than the tan delta peaks that occur at consistently higher temperatures, a finding that is consistent with a previous study. These transitions are attributed to the combination of the network's glass transition and PEO melting transition, respectively. It is noted that a second stepwise decrease in storage modulus at 89.2° C. was observed in DMA results, suggesting the presence of an order-disorder transition of the networks that is further confirmed by thermomechanical actuation data described below. This order-disorder (isotropization) transition has been noted in the DMA results of other liquid crystalline networks containing PEO spacers, and the temperature at which this transition occurs is similar to the isotropization endotherm observed in the DSC heating trace (FIGS. 6A and 6B).

Thermomechanical actuation of the dry LC networks was characterized at different stresses using DMA (FIG. 8). Upon heating under applied load (30 kPa), the film shows two stepwise contractions whose midpoints are located at 39.7° C. and 87.4° C. Upon cooling under load (30 kPa), the film shows two stepwise extensions at −7.8° C. and 25.1° C. Reversible extension and contraction when cooling and heating, respectively, under applied load has been shown to occur in both semicrystalline and liquid crystalline materials. Shape morphing can occur around the melting/recrystallization transitions of semi crystalline materials and around the LC-isotropic transition of LC materials. In N-5yHBP-PEO20-4.1, both events contribute to the two separate shape morphing events, where the lower temperature extension/contraction is aligned with the recrystallization/melting of transition of PEO and the higher temperature transition is aligned with the isotropization transition of the liquid crystals. The positions of these transitions are consistent with the DSC and the DMA data. As applied load increases, larger shape changes of N-5yHBP-PEO20-4.1 are evolved while the temperature at which the actuation occurs does not change, a finding that is consistent with literature.

Microstructure of 5yHBP-PEO20 Networks in the Dry and Hydrated States

Figure 9A:
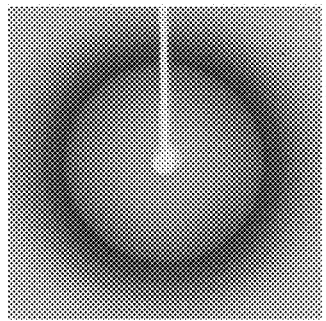
FIGS. 9A-9C show X-ray scattering of dry liquid crystalline networks.
Figure 9B:
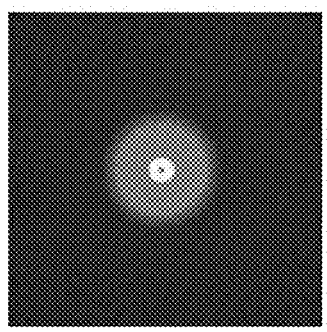
Figure 9C:
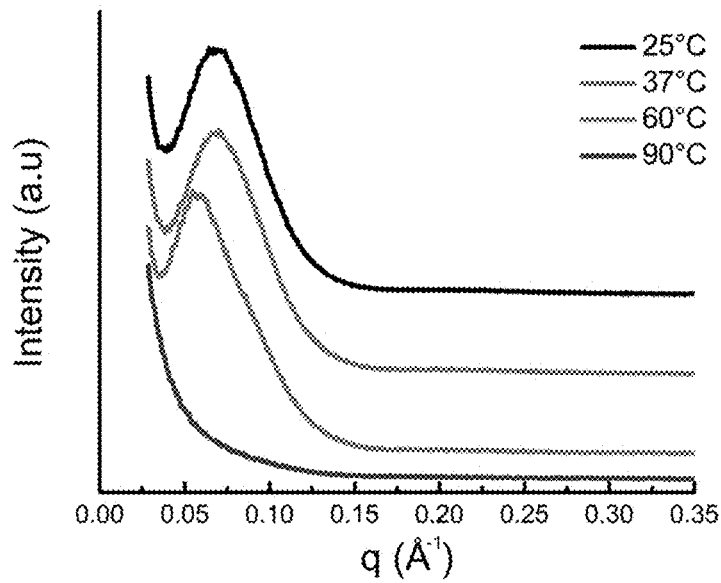
Figure 9D:
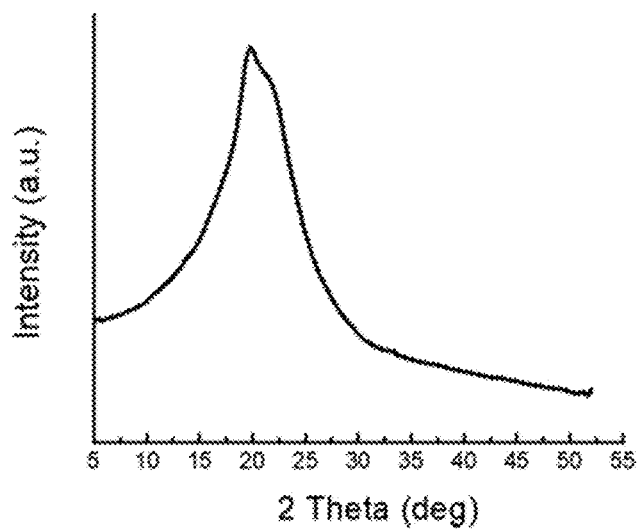
FIG. 9D shows 1D WAXS pattern of dry N-5yHBP-PEO20-4.1 acquired at 25° C.

X-ray scattering was used to characterize the microstructure of 5yHBP-PEO20 networks in the dry and hydrated states. The wide angle X-ray scattering (WAXS) pattern of N-5yHBP-PEO20-4.1 acquired at room temperature (FIG. 9A; 1D trace is shown in FIG. 9D) showed broad halos and one sharp ring centered at 2θ of 19.80°, which corresponds to d-spacing of 4.48 Å. The sharp ring at 19.80° (4.48 Å) is attributed to spacing between 5yHBP mesogens, which is similar to a mesogen spacing of 4.52 Å reported previously for alkyne-terminated mesogens in LCNs. Though the transition is sharp, there is no evidence of a melting transition, which further supports that this arises from liquid crystalline order. The broad halos are attributed to amorphous PEO structure from PEO spacers and crosslinkers. This confirms the DSC data that the PEO is not crystalline within the liquid crystalline network at this temperature (25° C.). In contrast, the 2D WAXS pattern of N-PEO75 (FIGS. 7A and 7B) shows crystalline PEO reflections.

To investigate longer-range ordering of N-5yHBP-PEO20-4.1, small angle X-ray scattering (SAXS) was used. The SAXS pattern of N-5yHBP-PEO20-4.1 acquired at room temperature (FIG. 9B) indicated one broad halo centered at $q=0.0685$ Å$^{-1}$ ($d=9.17$ nm), suggesting 5yHBP-PEO20 networks display longer-range ordering. SAXS measurements were also acquired at different temperatures to understand how the LC ordering changes as a function of temperature. Instrument limitations prevented the corresponding WAXS patterns from being acquired, as the reflections were blocked by the sample holder. The 1D SAXS data (FIG. 9c) shows that the halo is lost when temperature is raised between 60° C. and 90° C., which is in the same range as the isotropization temperature that was determined from thermomechanical data (FIGS. 6A and 6B). This longer range reflection is therefore linked to the liquid crystalline ordering in the material, though its length scale is larger than what is expected of a smectic liquid crystal layer (~2 nm). The origin of this reflection is therefore not clear, but it is envisioned that this could be driven by associations between mesogens or by a demixing/phase separation between PEO and the liquid crystals within the network. Demixing may also make the WAXS reflection corresponding to the spacing between mesogens appear sharper than expected for a LC material.

Figure 10A:
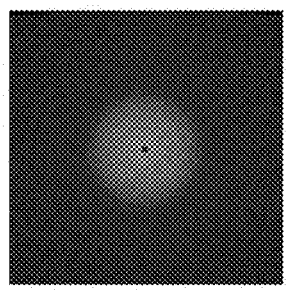
FIGS. 10A-10C show 2D SAXS of hydrated N-5yHBP-PEO20-4.1 at 25° C.
Figure 10:
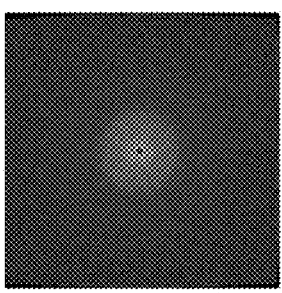
FIG. 10D shows 1D SAXS patterns of hydrated N-5yHBP-PEO20-4.1 measured at the temperatures noted therein.
Figure 10C:
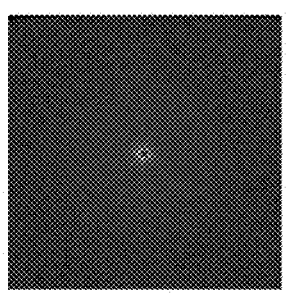
Figure 10D:
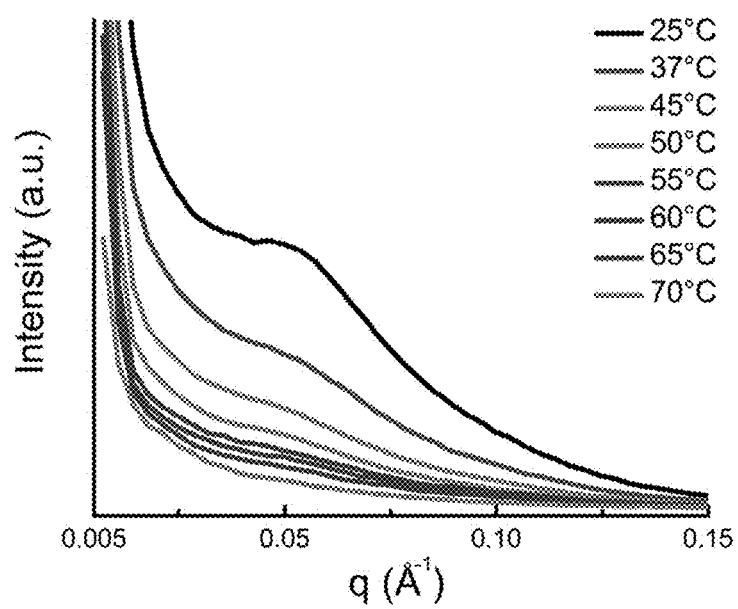
Figure 11:
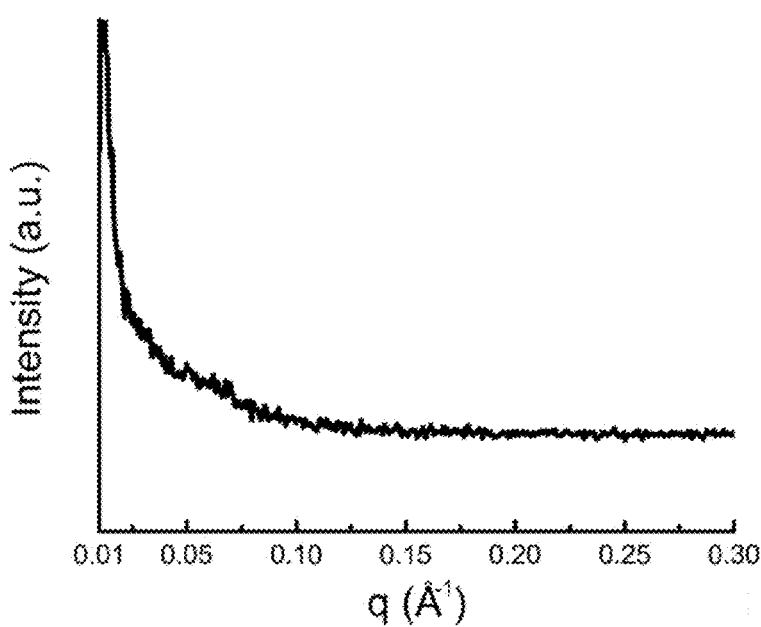
FIG. 11 shows 1D SAXS pattern of hydrated N-PEO75 acquired at 25° C.

As it was desired to use N-5yHBP-PEO20-4.1 as hydrogels, we questioned whether or not the networks could organize into liquid crystalline phases in the hydrogel state. The room temperature equilibrium water content of N-5yHBP-PEO20-4.1 was 405%. Mesogen spacing in hydrated networks cannot be characterized using WAXS because water has a large scattering signal in this region. The microstructure of hydrated LCNs was thus characterized using SAXS at varying temperatures. SAXS measurements of hydrated samples were conducted at different temperatures (FIGS. 10A-10D) to investigate how ordering changes with temperature. 2D SAXS patterns (FIGS. 10A-10C) showed that the broad halos associated with the LC mesophase disappeared between 37° C. and 55° C. The 1D SAXS traces (FIG. 10D) acquired from the patterns demonstrate the loss of the LC scattering ring upon heating hydrated LCNs, which is consistent with the isotropization transition. No peaks were observed in 1D SAXS pattern of hydrated N-PEO75 because this material lacks LC structure (FIG. 11). Compared to dry N-5yHBP-PEO20-4.1 at 25° C., the halo of hydrated LCNs is located at a d-spacing of 11.79 nm, which is larger than the d-spacing of dry samples (d-spacing=9.17 nm). Intensity is also lower in the hydrated state compared to dry materials, so water is involved with, but not required for, this reflection. This shift in q could be due to swelling of LC domains and/or an increase in the length scale of phase separation between hydrophilic PEO spacers and hydrophobic mesogens after water association with the networks. It should be noted that the temperature of isotropization observed in hydrated sample is also lower than the isotropization temperature of dry LCNs, indicating that the swollen gel has a weaker LC organization than dry networks. Overall, the longer-range ordering of hydrated LCNs and its dependence on temperature shows that the 5yHBP-PEO20 networks are thermotropic and maintain LC properties even in a highly swollen state. This conclusion is also supported by rheology data.

Shear Rheology Tests

Figure 12A:
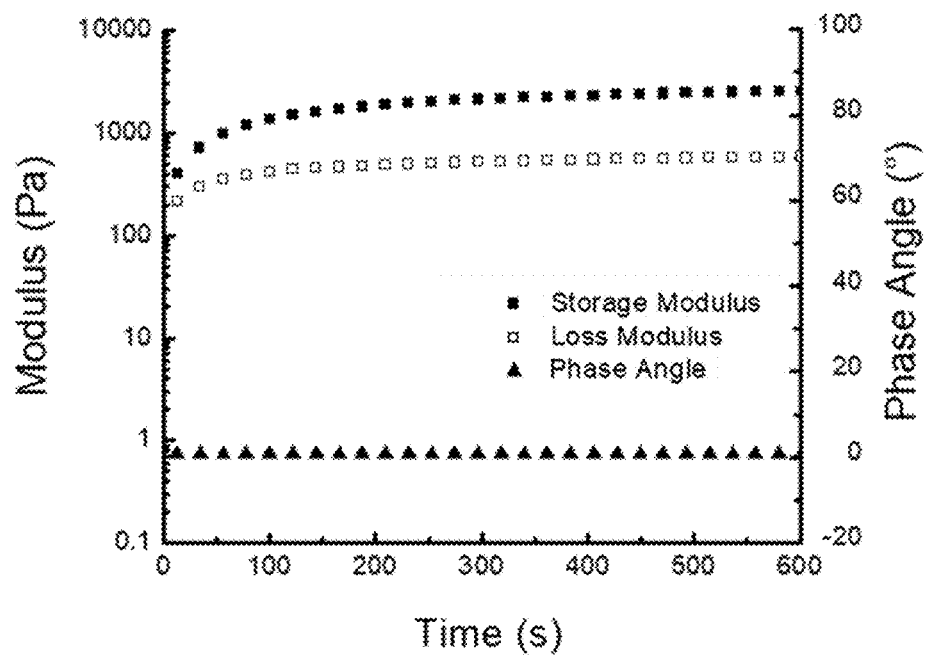
FIGS. 12A and 12B show modulus of hydrogels measured using shear rheology time sweeps at 15° C.
Figure 12B:
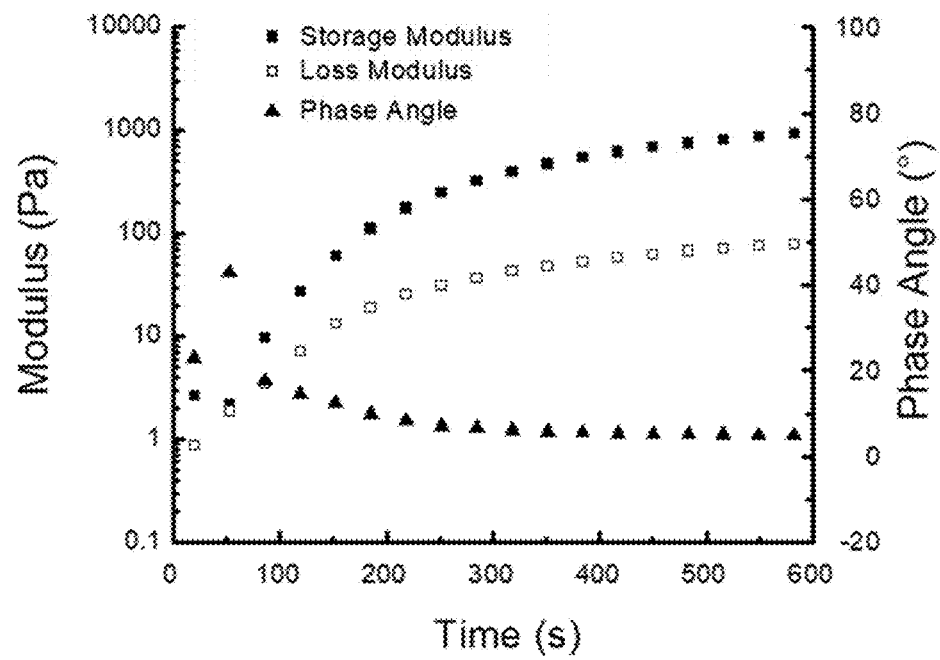
Figure 13A:
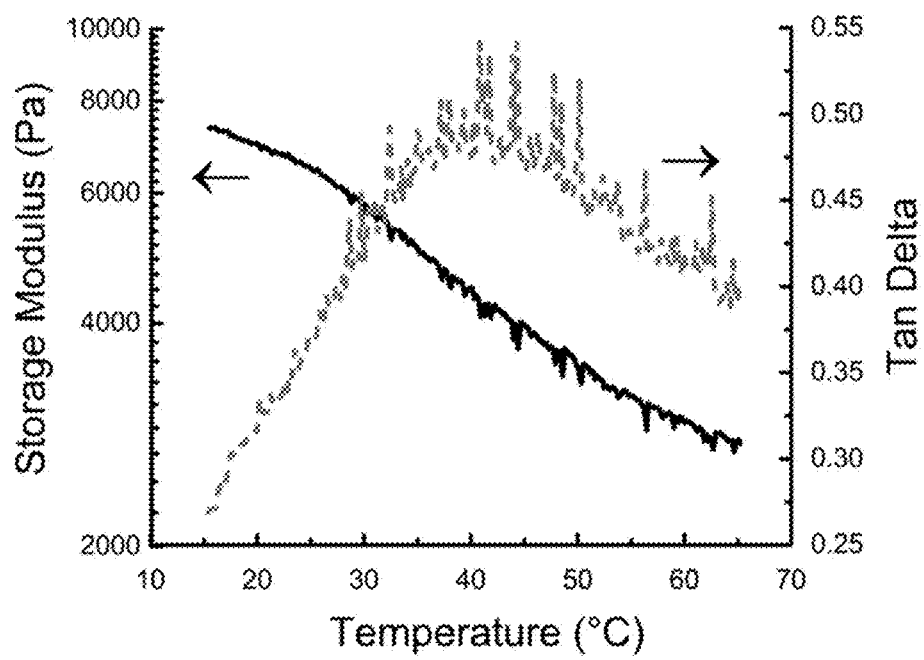
FIGS. 13A and 13B show shear storage modulus and tan delta as a function of temperature for hydrated N-5yHBP-PEO20-4.1 (a LC hydrogel, FIG. 13A) and hydrated N-PEO75 (a non-LC hydrogel, FIG. 13B).
Figure 13B:
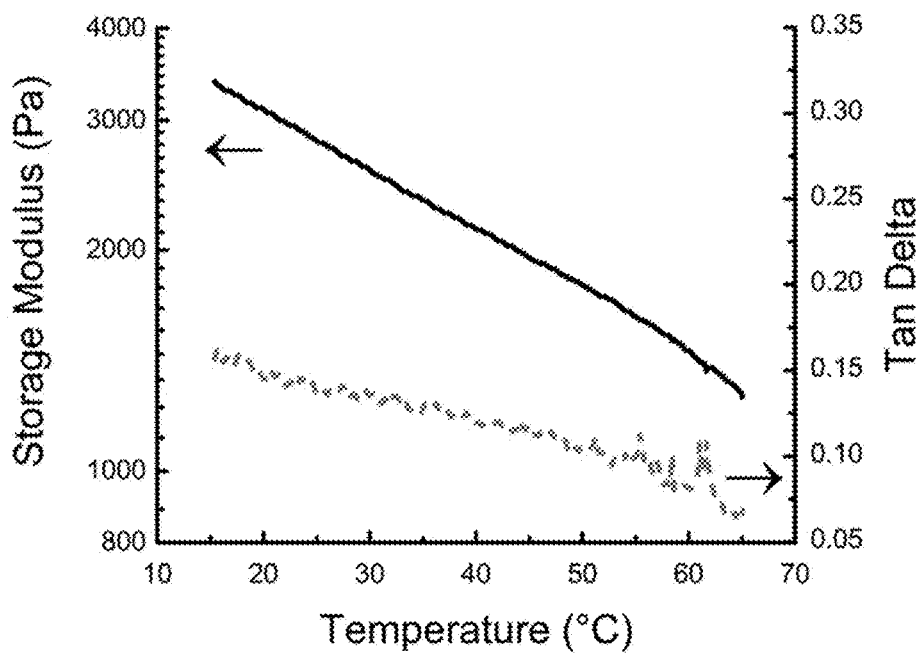

The gelation kinetics of liquid crystalline and non-liquid crystalline networks were quantified using small angle oscillatory shear time sweeps (FIGS. 12A and 12B). Due to rapid gelation kinetics (gelation occurs in <1 min at room temperature), these experiments were conducted subambiently at 15° C. Because the storage modulus was found to always exceed the loss modulus values, the time to gelation was taken as the time at which the storage modulus reached 90% maximum its maximum value, which was found to be at 390 s for N-5yHBP-PEO20-4.1 and 540 s N-PEO75 at 15° C. To assess if the networks organized into LC phases in the hydrated state, temperature sweeps were measured for N-5yHBP-PEO20-4.1 and N-PEO75 hydrogels. Both the storage modulus of LC and non-LC hydrogels decreased gradually with increasing temperature (FIGS. 13A and 13B), but a tan delta peak around 42° C. was observed for LC hydrogels and no tan delta peak was found for non-LC hydrogels. The tan delta peak occurs at a similar temperature as the disappearance of the SAXS scattering reflection of the N-5yHBP-PEO20-4.1 hydrogel (FIGS. 10A-10D) and is attributed to the LC hydrogel's isotropization transition. In this work, gels were designed be LC without a phase transition during cell culture to assess viability and proliferation relative to non-LC gels. It may be possible to tune composition to be able to induce isotropization during culture, similar to how shape memory materials have been triggered to recover during cell culture.

Example 2. Biological Studies

Cell Encapsulation

Human mesenchymal stem cells (hMSC, 320,000 cells) were suspended in 20.0 µL of 13 wt % 4-arm DBCO-PEO dissolved in sterile, complete culture medium (DMEM containing 10% FBS and 1% anti-anti). 10 wt % 5yHBP-PEO20-4.1 polymer dissolved in sterile, complete medium before adding 44.0 µL of the solution to the cell suspension and gently pipetting to mix. A 25.0 µL aliquot of the reacting mixture was placed over an area of 24 mm$^2$ on top of a polystyrene coverslip, which was then placed in the bottom of a 24-well tissue culture plate. The solution gelled, and after 10 minutes the well was flooded with 0.45 mL complete DMEM. Cells were cultured at 37° C. in a 5% $CO_2$ incubator. For encapsulating hMSCs in N-PEO75 networks, 15 wt % PEO75-azide in complete medium (23.0 µL) was added to 20.0 µL of 13 wt % 4-arm DBCO-PEO in complete medium that contained hMSCs (215,000 cells). The mixture was gently pipetted up and down to obtain a uniform suspension. The same steps as described above were then followed to complete gelation and to maintain the cells in culture.

Cell Viability by Live/Dead Staining

A working solution was prepared to contain 4 µM Calcein AM and 1 µL/mL ethidium homodimer-1 in PBS. The working solution (200 µL) was added to the top of each gel after 24 h in culture. After 20 min staining at 25° C., cells were imaged using Nikon A1R confocal microscope with 488 nm Argon laser and 561 nm diode laser. Images were analyzed by ImageJ (version 1.52p) from National Institutes of Health (Bethesda, Md.).

Proliferation Assay

Human mesenchymal stem cells were encapsulated in LC gels and non-LC gels at 2,500,000 cells/mL gel using the encapsulation method described above. An alamarBlue working solution was prepared by mixing complete medium with alamarBlue reagent in a 10/1 volume ratio. The working solution (0.45 ml per well) was added to cellularized gels, acellular gels, and blank wells lacking gels 24 h after encapsulation (Day 1). The gels were incubated with this solution for 5 h at 37° C. and 5% $CO_2$ before removing an aliquot of the supernatant and transferring to 96-well black opaque plate. Fluorescence (Ex 560 nm, Em 590 nm) was measured on a Synergy HT microplate reader equipped with Gen5 (version 1.04.5) from BioTeck Instruments (Winooski, Vt.). The remaining alamarBlue working solution was aspirated and the gels were washed using sterile PBS before replacing with complete medium. The assay was repeated at Day 4, Day 6, and Day 8. The fluorescence from cellular groups was normalized by the acellular groups, where higher values suggested more live cells in gels. The proliferation ratio of each day was calculated by dividing normalized fluorescence of the timepoint by normalized fluorescence from Day 1.

Mesenchymal Stem Cell Viability and Proliferation within Hydrogels

Strain-promoted alkyne-azide cycloaddition (SPAAC) has been used to encapsulate cells within PEO-containing gels and to modify living cells, but it was not known how the presence of the liquid crystalline phase would affect the viability and proliferation of encapsulated cells. hMSCs were used to demonstrate that primary cells can be encapsulated within the gels and may also enable differentiation studies to be conducted in the future. Live-dead staining imaged with confocal microscopy 24 hours after encapsulation was used to assess viability of human mesenchymal stem cells (hMSCs) encapsulated within the LC and non-LC hydrogels. The green fluorescence from live cells is dominant in the images compared to the red fluorescence from dead cells, and counting the number of cells in each channel permitted the calculation of cell viability after encapsulation. The viability of hMSCs was found to be 72% and 70% for N-5yHBP-PEO20-4.1 and N-PEO75, respectively (FIGS. 14A and 14B), indicating that liquid crystallinity does not affect cell viability at this timepoint. More clumping of cells was observed in the images of PEO75 networks than was observed in N-5yHBP-PEO20-4.1. This behavior was found to be reproducible, and therefore it is attributed to the properties of the materials, rather than the encapsulation technique. The proliferation of hMSCs in LC and non-LC hydrogels was also compared using an alamarBlue assay, which measures mitochondrial activity. LC hydrogels showed significantly faster proliferation compared to the non-LC gels over the culture period investigated (FIG. 15). While both types of gels supported the proliferation of cells, the number of live cells in LC gels increased by 57.2% in 8 days, while the number of live cells in non-LC gels only increased by 18.3% in the same period.

Taken together, LC gels were found to support in vitro culture of hMSCs and demonstrate potential for enhanced proliferation compared to non-LC hydrogel controls. As the polymer compositions were designed so that the resulting gels had similar storage modulus, bulk stiffness is not expected to be the main cause for this difference in cell behavior. In addition, although local order within an LC phase can be high, these gels were not oriented on the bulk scale in a particular dimension. It is envisioned that cell function in LC gels may be affected by differences in the phase organization and/or structures present within the gel, the anisotropy of the polymer chains that may affect how cells sense local versus bulk viscoelasticity, how cells sense hydrophobicity within the gels, or some other factor.

In conclusion, a new approach to synthesize main-chain liquid crystalline hydrogels in aqueous media is provided herein, which permits cell encapsulation and 3D culture in LC hydrogels. Tuning the strength of the mesogen's mesophase, the length of the hydrophilic oligomer, and the ratio of reactants resulted in the synthesis of LC polymers with varying molecular weights and degrees of aqueous solubility. The polymers were crosslinked using SPAAC, and the thermal, mechanical, and microstructural properties of the networks were characterized. The networks formed LC phases with longer range order in both the dry and hydrogel states. Human mesenchymal stem cells encapsulated in the hydrogels displayed good viability that was not found to be dependent on LC phase 24 h after encapsulation. In some results, hMSC morphology was found to be more spread in the LC gels compared to the non-LC gels. Further, encapsulated hMSCs were found to proliferate significantly faster in LC hydrogels compared to non-LC hydrogels. Thus, main-chain liquid crystalline polymers as disclosed herein may be crosslinked in aqueous media to form a new hydrogel platform, which may provide liquid crystalline order to affect cell and protein function in tissue constructs.

It is understood that the foregoing detailed description and accompanying examples are merely illustrative and are not to be taken as limitations upon the scope of the invention, which is defined solely by the following claims.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:
1. A polymer of formula (I),

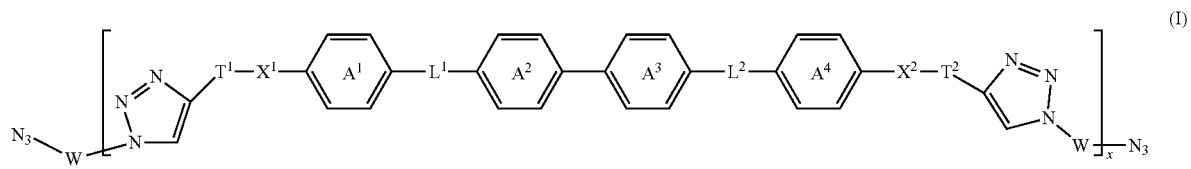

wherein
A¹, A², A³, and A⁴ are each independently a phenyl optionally substituted with 1, 2, 3, or 4 $R^a$;
L¹, L², X¹, and X² are each independently O, NH, C(O), C(O)O, C(O)NH, or OC(O)NH;
T¹ and T² are each independently $C_{1-6}$alkylene;
W is $W^0$-L; wherein $W^0$ is selected from the group consisting of a polyether, a polyester, a polyamide, a polysiloxane, a polyurethane, and a combination thereof; and wherein L is a bond or —S—S—;

$R^a$ at each occurrence is independently —NH₂, —OH, —COOH, —CHO, halogen, cyano, —Oalkyl, —NHalkyl, —N(alkyl)₂, —C(O)alkyl, —C(O)Oalkyl, —OC(O)alkyl, —C(O)NHalkyl, —NHC(O)alkyl, or an alkyl optionally substituted with —NH₂, —OH, —COOH, or —CHO; and
x is 1 to 100.
2. The polymer of claim 1, wherein L is —S—S—.
3. The polymer of claim 1, having a structure of formula (I-a),

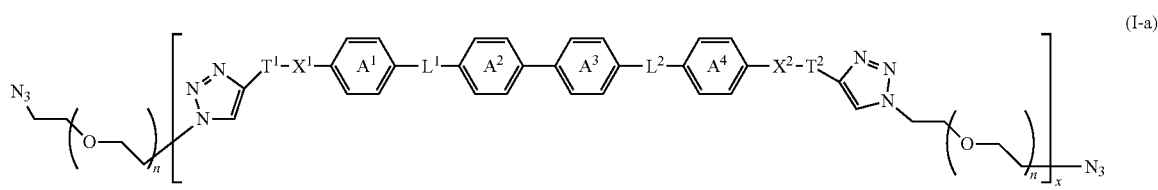

wherein
A¹, A², A³, A⁴, L¹, L², X¹, X², T¹ T², and x are as defined in formula (I); and
n is 3 to 100.
4. The polymer of claim 1, having a structure of formula (I-a-1),

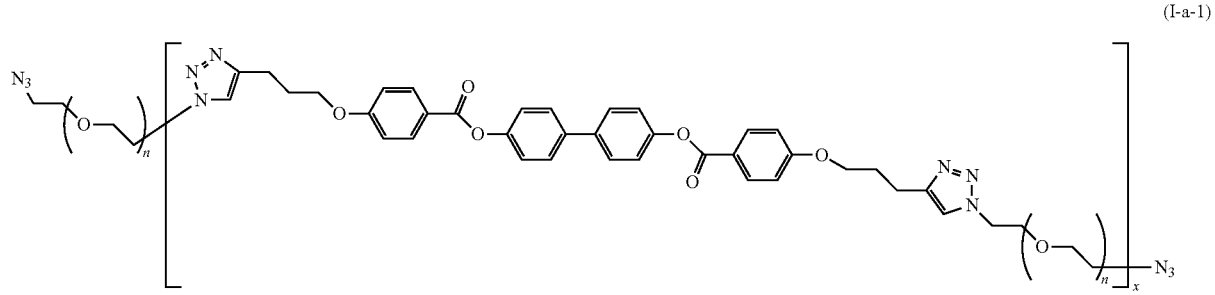

wherein x and n are as defined in formula (I-a).

5. The polymer of claim 3, wherein x is 1 to 10, and n is 15 to 25.

6. The polymer of claim 1, having a molecular weight of about 2 kDa to about 20 kDa.

7. A crosslinked polymer comprising a moiety of formula (II),

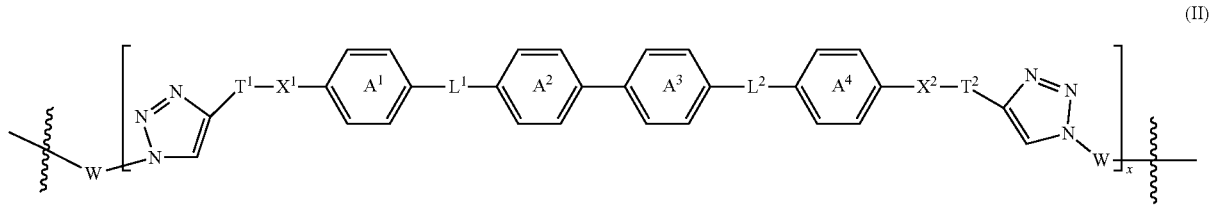

wherein
$A^1$, $A^2$, $A^3$, and $A^4$ are each independently a phenyl optionally substituted with 1, 2, 3, or 4 $R^a$;
$L^1$, $L^2$, $X^1$, and $X^2$ are each independently O, NH, C(O), C(O)O, C(O)NH, or OC(O)NH;
$T^1$ and $T^2$ are each independently $C_{1-6}$alkylene;
W is $W^0$-L; wherein $W^0$ is selected from the group consisting of a polyether, a polyester, a polyamide, a polysiloxane, a polyurethane, and a combination thereof; and wherein L is a bond or —S—S—;
$R^a$ at each occurrence is independently —NH$_2$, —OH, —COOH, —CHO, halogen, cyano, —Oalkyl, —NHalkyl, —N(alkyl)$_2$, —C(O)alkyl, —C(O)Oalkyl, —OC(O)alkyl, —C(O)NHalkyl, —NHC(O)alkyl, or an alkyl optionally substituted with —NH$_2$, —OH, —COOH, or —CHO;
x is 1 to 100; and
at least one terminal indicated by ⌇ is attached to a crosslinker.

8. The polymer of claim 7, wherein L is —S—S—.

9. The crosslinked polymer of claim 7, wherein the moiety has a structure of formula (II-a),

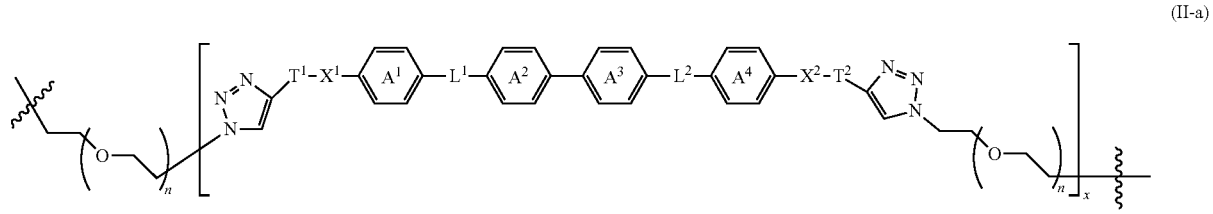

wherein
$A^1$, $A^2$, $A^3$, $A^4$, $L^1$, $L^2$, $X^1$, $X^2$, $T^1$ $T^2$, and x are as defined in formula (II); and
n is 3 to 100.

10. The crosslinked polymer of claim 7, wherein the moiety has a structure of formula (II-a-1),

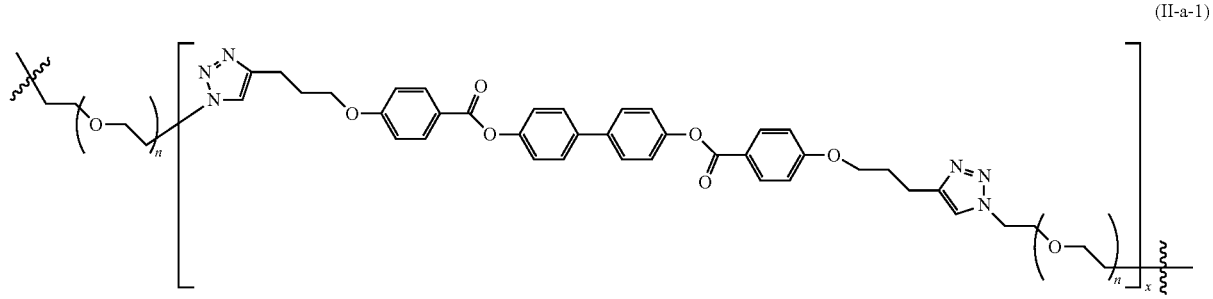

wherein x and n are as defined in formula (II-a).

11. The crosslinked polymer of claim 9, wherein x is 1 to 10, and n is 15 to 25.

12. The crosslinked polymer of claim 7, wherein the moiety has a molecular weight of about 2 kDa to about 20 kDa.

13. The crosslinked polymer of claim 7, wherein the crosslinker is a dibenzocyclooctyne (DBCO) derivative.

14. The crosslinked polymer of claim 7, wherein the crosslinked polymer forms a main-chain liquid crystalline (LC) hydrogel in an aqueous medium.

15. A method of preparing a crosslinked polymer, comprising reacting the polymer of claim 1 with a crosslinker, thereby forming a crosslinked polymer.

16. A crosslinked polymer produced by crosslinking the polymer of claim 1.

17. A method of culturing a plurality of cells, comprising
crosslinking the polymer of claim 1 by a crosslinker in a medium in which the cells are dispensed, thereby forming a three-dimensional network of the crosslinked polymer and encapsulating the cells in the three-dimensional network; and
culturing the encapsulated cells.

18. The method of claim 17, wherein the crosslinking comprises
mixing the crosslinker and the cells in the medium to form a mixture; and
adding the polymer to the mixture.

19. The method of claim 17, wherein the cells comprise a blood cell, a muscle cell, a heart cell, a liver cell, a kidney cell, a skin cell, a neuron, a stem cell, or a combination thereof.

20. The method of claim 17, wherein the cells comprise a human mesenchymal stem cell.

* * * * *